US011976337B2

(12) United States Patent
Jost et al.

(10) Patent No.: US 11,976,337 B2
(45) Date of Patent: May 7, 2024

(54) METHODS FOR DETECTION OF INFLUENZA IN SAMPLES

(71) Applicant: GEN-PROBE INCORPORATED, San Diego, CA (US)

(72) Inventors: Matthias Jost, San Diego, CA (US); Pamela Douglass, Kansas City, MO (US); Daniel P. Kolk, Ramona, CA (US); Mehrdad R. Majlessi, Escondido, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 695 days.

(21) Appl. No.: 16/488,909

(22) PCT Filed: Mar. 23, 2018

(86) PCT No.: PCT/US2018/023995
§ 371 (c)(1),
(2) Date: Aug. 26, 2019

(87) PCT Pub. No.: WO2018/175868
PCT Pub. Date: Sep. 27, 2018

(65) Prior Publication Data

US 2020/0048721 A1 Feb. 13, 2020

Related U.S. Application Data

(60) Provisional application No. 62/476,659, filed on Mar. 24, 2017.

(51) Int. Cl.
*C12Q 1/70* (2006.01)

(52) U.S. Cl.
CPC ............... *C12Q 1/701* (2013.01); *C12Q 1/70* (2013.01); *C12Q 2561/101* (2013.01); *C12Q 2563/107* (2013.01); *C12Q 2600/16* (2013.01)

(58) Field of Classification Search
None
See application file for complete search history.

(56) References Cited

U.S. PATENT DOCUMENTS

| | | | | |
|---|---|---|---|---|
| 4,683,202 | A * | 7/1987 | Mullis | C12Q 1/686 435/317.1 |
| 6,015,664 | A | 1/2000 | Henrickson et al. | |
| 8,354,230 | B2 | 1/2013 | Chen et al. | |
| 9,624,555 | B2 | 4/2017 | Hellyer et al. | |
| 2010/0055672 | A1 | 3/2010 | Saghbini | |
| 2010/0273156 | A1 | 10/2010 | Hellyer et al. | |
| 2013/0267429 | A1 * | 10/2013 | Gardner | C12Q 1/6876 506/8 |
| 2014/0309138 | A1 | 10/2014 | Poetter et al. | |
| 2016/0273057 | A1 | 9/2016 | Roth | |
| 2019/0002994 | A1 | 1/2019 | Jeon et al. | |

FOREIGN PATENT DOCUMENTS

| | | | | | |
|---|---|---|---|---|---|
| CN | 102337352 | | * | 2/2012 | |
| CN | 105400907 | | * | 3/2016 | |
| JP | 2012532627 | A | | 12/2012 | |
| JP | 201522104 | A | | 12/2015 | |
| JP | 2016131498 | A | | 7/2016 | |
| WO | WO-2007064758 | A2 | * | 6/2007 | C12Q 1/701 |
| WO | WO-2007130519 | A2 | * | 11/2007 | C12Q 1/70 |
| WO | WO-2008140513 | A1 | * | 11/2008 | C12Q 1/70 |
| WO | WO 2009/085733 | A1 | | 7/2009 | |
| WO | WO 2009/085733 | A4 | | 7/2009 | |
| WO | WO 2013/006720 | A2 | | 1/2013 | |
| WO | WO-2016004539 | A1 | * | 1/2016 | B01L 3/502715 |
| WO | WO 2016/028312 | A1 | | 2/2016 | |
| WO | WO-2016028312 | A1 | * | 2/2016 | C12Q 1/701 |

OTHER PUBLICATIONS

Wesenbeeck (Journal of Clinical Microbiology (2013) vol. 51, pp. 2977-2985).*

Diffenbach (PCR methods and Applications (1993) vol. 3, pp. S30-S37).*

Roux et al(PCR Methods and Applications (1995) vol. 4, pp. s185-s194).*

Leal (Brazilian Journal of Microbiology 44, 3, 901-904 (2013).*

NCBI Database. GenBank Accession No. KC355801.1, Jan. 13, 2013, National Library of Medicine, NIH, available via URL: <ncbi.nlm.nih.gov/nuccore/KC355801.1/> (Year: 2013).*

European Examination Report dated Sep. 2, 2021 in corresponding application No. 18718029.4 (9 pages).

De-Paris, et al., "Optimization of one-step duplex real-time RT-PCR for detection of influenza and respiratory syncytial virus in nasopharyngeal aspirates," J Virol Methods, 186(1-2):189-92, doi: 10.1016/j.jviromet.2012.07.008, Epub Jul. 13, 2012, (Dec. 2012).

Jost, et al., "The modular approach to respiratory syndromic testing with the fully-automated novel Panther Fusion System," Journal of Clinical Virology, 82S, S1-S142, Abstract No. 171, Presentation at ESCV 2016: Poster 22, (2016).

Mahony, et al., "Development of a respiratory virus panel test for detection of twenty human respiratory viruses by use of multiplex PCR and a fluid microbead-based assay," J Clin Microbiol, 45(9):2965-70, doi: 10.1128/JCM.02436-06, Epub Jun. 27, 2007, (Sep. 2007).

Mahony, "Detection of respiratory viruses by molecular methods," Clin Microbiol Rev., 21(4):716-47, doi: 10.1128/CMR.00037-07, (Oct. 2008).

(Continued)

*Primary Examiner* — Carla J Myers

(74) *Attorney, Agent, or Firm* — Jeffrey E. Landes; Alston & Bird LLP

(57) ABSTRACT

This disclosure concerns amplification primers, hybridization assay probes, compositions containing such primers and probes, and associated reagents, kits, and methods, that can be used to analyze samples for the presence of Influenza A virus, Influenza B virus, Respiratory Syncytial Virus A, and/or Respiratory Syncytial Virus B target nucleic acids.

9 Claims, No Drawings

Specification includes a Sequence Listing.

(56) References Cited

OTHER PUBLICATIONS

Adachi, et al., "Comparison of the IMDx influenza A virus, influenza B virus, and respiratory syncytial virus A/B assay on the m2000 platform with real-time reverse transcriptase PCR assays," J Clin Microbiol, 52(12):4441-2,doi: 10.1128/JCM.02565-14, Epub Oct. 1, 2014, (Dec. 2014).
Van Wesenbeeck, et al., "Comparison of the FilmArray RP, Verigene RV+, and Prodesse ProFLU+/FAST+ multiplex platforms for detection of influenza viruses in clinical samples from the 2011-2012 influenza season in Belgium," J Clin Microbiol, 51(9):2977-85, doi: 10.1128/JCM.00911-13, Epub Jul. 3, 2013, (Sep. 2013).
Raymond, et al., "Comparison of automated microarray detection with real-time PCR assays for detection of respiratory viruses in specimens obtained from children," J Clin Microbiol, 47(3):743-50, doi: 10.1128/JCM.01297-08, Epub Jan. 21, 2009, (Mar. 2009).
Li, et al., "The development of a GeXP-based multiplex reverse transcription-PCR assay for simultaneous detection of sixteen human respiratory virus types/subtypes," BMC Infect Dis, 12:189, doi: 10.1186/1471-2334-12-189, (Aug. 14, 2012).
Hologic, Inc., Panther Fusion® System Assay Performance, Flu A/B/RSV, AW-16832 Rev. 001, (Sep. 2017).
Japanese Office Action dated Sep. 8, 2020 in corresponding application No. 2019-552249 (12 pages).
Canadian Office Action dated Jun. 11, 2020 in corresponding application No. 3,055,427 (4 pages).
International Preliminary Report on Patentability dated Sep. 24, 2019 in corresponding PCT application PCT/US2018/023995 (10 pages).
Japanese Office Action dated May 17, 2021 in corresponding application No. 2019-552249 (15 pages).

* cited by examiner

METHODS FOR DETECTION OF INFLUENZA IN SAMPLES

CROSS REFERENCE TO RELATED APPLICATIONS

This application is a national stage entry of PCT/US2018/023995, filed Mar. 23, 2018, which claims priority under 35 U.S.C. § 119 of U.S. Provisional Application 62/476,659, filed Mar. 24, 2017, the contents of which are incorporated herein by reference.

REFERENCE TO SEQUENCE LISTING

This application includes an electronic sequence listing in a file named "536045_SEQLST.TXT", created Aug. 26, 2019 and containing 66,165 bytes, which is hereby incorporated by reference.

BACKGROUND

Field

The present disclosure relates to the field of biotechnology. More specifically, the disclosure relates to compositions, including kits and reagents, and methods for analysis of samples to detect viral pathogens, particularly Influenza Virus and Respiratory Syncytial Virus.

Background

Influenza is an acute respiratory illness in humans caused by infection with the Influenza (Flu) virus, primarily types A and B. Influenza A viruses are further categorized into subtypes based on two major surface protein antigens, hemagglutinin (H), and neuraminidase (N). Influenza B viruses are not categorized into subtypes. The Influenza viruses are RNA viruses in the family Orthomyxoviridae. Each of Influenza types A and B (Flu A and Flu B, respectively) is a separate genus containing one species and a large number of sub-species.

Influenza epidemics occur yearly around the world. Although both Flu types A and B circulate in the population, type A is usually dominant. These yearly epidemics are partly due to antigenic variation in the H and N surface proteins of the virus. Transmission of influenza is primarily via airborne droplet (coughing or sneezing). Symptoms arise on average 1 to 2 days post-exposure and include fever, chills, headache, malaise, cough, and coryza. Gastrointestinal symptoms such as nausea, vomiting, and diarrhea can occur, primarily in young children. Complications due to influenza include pneumonia, which can cause increased morbidity and mortality in pediatric, elderly, and immune-compromised populations. In the United States, it is estimated that influenza results in more than 200,000 hospitalizations and up to 36,000 deaths annually. Large influenza outbreaks, or pandemics, occur rarely. In the $20^{th}$ Century, three influenza pandemics occurred, in 1918, 1958, and 1968, each causing millions of deaths worldwide. Influenza may also affect other animals, including pigs, horses and birds.

Respiratory syncytial virus (RSV) is the leading cause of lower respiratory tract infections in infants and children. Like Influenza, RSV is an RNA virus. RSV is a member of the family Paramyxoviridae, in the genus Orthopneumovirus. There are 2 types of RSV, A and B, which are differentiated based on antigenic and surface protein variations.

Most yearly epidemics contain a mix of RSV A and RSV B, but one subgroup can dominate during a season. RSV infection can cause severe respiratory illness among all ages but is more prevalent in pediatric, elderly, and immune-compromised populations. RSV can infect up to 80% of children less than 1 years of age. Bronchiolitis and pneumonia are the major clinical complications in infants and young children, resulting in an estimated 51,000-82,000 hospital admissions per year in the United States. RSV infection is also an important cause of severe respiratory disease and substantial number of deaths in the elderly, with an estimated annual cost of $150 to $680 million for RSV pneumonia hospitalizations.

Given the morbidity, mortality, and economic costs associated with Influenza and RSV infections, there clearly exists a need for improved detection of these pathogens. This disclosure addresses this and other needs.

BRIEF DESCRIPTION

This disclosure provides compositions, including kits and reagents, and methods for in vitro diagnostic analysis of Influenza A Virus (Flu A), Influenza B Virus (Flu B), Respiratory Syncytial Virus type A (RSV A) or Respiratory Syncytial Virus type B (RSV B) nucleic acids in a sample. Preferably the in vitro diagnostic analysis utilizes polymerase chain reactions (PCR), though other in vitro assay methodologies are contemplated for use with the disclosed compositions. A particularly useful in vitro assay for use with the Flu A, Flu B, RSV A or RSV B target nucleic acids is a reverse transcription PCR assay, as these target nucleic acids are RNA viruses. Conveniently, in vitro amplification assays can performed simultaneously with in vitro detection assays (real-time PCR). Thus, a particularly useful and convenient in vitro assay for use with the Flu A, Flu B, RSV A or RSV B target nucleic acids is a real-time, reverse transcription PCR assay.

It should be noted that, as used in this specification and the appended claims, the singular form "a," "an," and "the" include plural references unless the context clearly dictates otherwise. Thus, for example, reference to "an oligonucleotide" includes a plurality of oligonucleotides and the like. The conjunction "or" is to be interpreted in the inclusive sense, i.e., as equivalent to "and/or," unless the inclusive sense would be unreasonable in the context.

It will be appreciated that there is an implied "about" prior to the temperatures, concentrations, times, etc. discussed in the present disclosure, such that slight and insubstantial deviations are within the scope of the present teachings herein. In general, the term "about" indicates insubstantial variation in a quantity of a component of a composition not having any significant effect on the activity or stability of the composition. All ranges are to be interpreted as encompassing the endpoints in the absence of express exclusions such as "not including the endpoints"; thus, for example, "within 10-15" includes the values 10 and 15 and all whole and partial (when applicable) values there between.

Unless specifically noted, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims). "Consisting essentially of" means that additional component(s), composition(s) or method step(s) that do not materially change the basic and novel characteristics of the compositions and methods described herein may be included in those compositions or methods. Such characteristics include the ability to detect a target nucleic acid present in a sample with specificity that distinguishes the target nucleic acid from other known respiratory pathogens. Any component(s), composition(s), or method step(s) that have a material effect on the basic and novel characteristics of the present disclosure would fall outside of this term.

The term "complement" refers to a nucleic acid molecule that comprises a contiguous nucleotide sequence that is complementary to a contiguous nucleic acid sequence of another nucleic acid molecule (for standard nucleotides A:T, A:U, C:G). For example 5'-AACTGUC-3' is the complement of 5'-TTGACAG-3'. Two nucleic acid sequences are "sufficiently complementary" when, their respective contiguous nucleic acid sequences are at least 70% complementary. (see, e.g., See Sambrook, et al., Molecular Cloning, A Laboratory Manual, $2^{nd}$ ed. (Cold Spring Harbor Laboratory Press, Cold Spring Harbor, N.Y., 1989)).

"Perfectly matched" in reference to a nucleic acid duplex means that the poly- or oligonucleotide strands making up the duplex form a double-stranded structure, or region of double-stranded structure, with one another such that every nucleotide (or nucleotide analogue) in each strand undergoes Watson-Crick base-pairing with a nucleotide in the other strand in the duplexed (i.e., hybridized) region. The term also comprehends the pairing of nucleoside analogues, such as deoxyinosine, nucleosides with 2-aminopurine bases, and the like. Conversely, a "mismatch" in a nucleic acid duplex means that one or more pairs of nucleotides in the duplex fail to undergo Watson-Crick base-pairing.

By "substantially homologous," "substantially corresponding", or "substantially corresponds" is meant a nucleic acid molecule comprises a contiguous nucleic acid sequence that is at least 70% homologous to a contiguous nucleic acid sequence of another nucleic acid molecule.

A "sample" or "biological sample" is any tissue or polynucleotide-containing material obtained from a human, animal, or environmental sample and which may contain a target nucleic acid. Biological samples include peripheral blood, mucus, plasma, serum, saliva, cerebrospinal fluid, urine, or other body fluid, bone marrow, or other organ, biopsy tissue, or other materials of biological origin, as well as solutions or compositions containing materials of biological origin, for example, a bronchial lavage fluid. Samples can be obtained from a number of sources, including a clinical source wherein the sample is collected in order to determine the presence or absence of a target nucleic acid in the sample and in turn provide a patient with a diagnosis. A sample may be chemically and/or mechanically treated to disrupt tissue or cell structure, thereby releasing intracellular components into a solution.

The term "nucleotide" is defined herein to include both nucleotides and nucleosides, including deoxyribonucleotides (e.g., dATP, dCTP, dGTP, dTTP), ribonucleotides (e.g., rATP, rCTP, rGTP, rUTP), and analogues thereof. Nucleotides comprise a purine or pyrimidine base linked glycosidically to a ribose or a deoxyribose sugar and a phosphate group attached to the ribose or deoxyribose sugar. Nucleosides comprise a purine or pyrimidine base linked glycosidically to a ribose or a deoxyribose sugar, but lack the phosphate residues that are present in a nucleotide. Nucleotides and nucleosides, as used herein, refer to a monomer of DNA or RNA, respectively. (See e.g., Kornberg and Baker, DNA Replication, $2^{nd}$ Ed. (Freeman, San Francisco, 1992)).

The term "analogue", in reference to a chemical compound, refers to compound having a structure similar to that of another one, but differing from it in respect of one or more different atoms, functional groups, or substructures that are removed or replaced with one or more other atoms, functional groups, or substructures. In the context of a nucleotide or nucleoside, an analog refers to a compound that, like the nucleotide/side of which it is an analog, can be incorporated into a nucleic acid molecule (e.g., a primer, a probe and/or an amplification product). Nucleotide/side analogs are commonly added to synthetic oligonucleotides (such as primers and probes) using phosphoramidite chemistry techniques and devices. Nucleotide/side analogs are commonly added to amplification products by including the analog in a reaction mixture wherein a suitable polymerase, for example, a DNA polymerase, will incorporate the analog into the amplification product. Nucleotide/side (hereinafter "nucleotide") analogs include synthetic nucleotides having modified base moieties and/or modified sugar moieties and/or modified phosphate groups, see, e.g., Scheit, Nucleotide Analogues (John Wiley, New York, 1980); Uhlman and Peyman, Chemical Reviews, 90:543-584 (1990), or the like. Such analogues include synthetic nucleosides designed to enhance binding properties, reduce complexity, increase specificity, and the like.

"DNA" refers to deoxyribonucleic acid, a polymer of deoxyribonucleotides linked by phosphodiester bonds. DNA can be single-stranded (ssDNA) or double-stranded (dsDNA), and can include both single and double-stranded (or "duplex") regions. "RNA" refers to ribonucleic acid, a polymer of ribonucleotides linked by phosphodiester bonds. RNA can be single-stranded (ssRNA) or double-stranded (dsRNA), and can include both single and double-stranded (or "duplex") regions. Single-stranded DNA (or regions thereof) and ssRNA can, if sufficiently complementary, hybridize to form double-stranded complexes (or regions). By "RNA equivalent", "DNA equivalent", "RNA equivalent bases" and "DNA equivalent bases" is meant RNA and DNA molecules having similar complementary base pair hybridization properties. RNA and DNA equivalents have different sugar moieties (i.e., ribose versus deoxyribose) and may differ, for example, by the presence of uracil in RNA and thymine in DNA. The differences between RNA and DNA equivalents do not contribute to differences in homology (or sequence identity) because the equivalents have the same degree of complementarity to a particular sequence.

The terms "polynucleotide" or "oligonucleotide" (used synonymously herein) mean a multimeric compound comprising two or more joined RNA nucleotides, DNA nucleotides, analogs of RNA nucleotides, analogs of DNA nucleotides, or combinations thereof. Polynucleotides can include other molecules that may be present in a joined sequence of nucleotides and that do not prevent hybridization of the polynucleotide with a second molecule having a complementary sequence. For example, a polynucleotide can include two or more joined nucleotides on a first side of a linker molecule and two or more joined nucleotides on a second side of the linker molecule, as is often the configuration of a molecular torch. Polynucleotides are preferably a polymeric chain of from 10 to 200 contiguous nucleotides. Polynucleotides may be purified from naturally occurring sources, but preferably are synthesized using any of a variety of well-known enzymatic or chemical methods. Whenever an oligonucleotide (or other nucleic acid) is represented by a sequence of letters, such as "ATGCUCTG", unless otherwise indicated, it will be understood that the nucleotides are in 5'-3' orientation from left to right and that "A" denotes adenosine (dATP/rATP) or an analogue thereof, "C" denotes cytidine (dCTP/rCTP) or an analogue thereof, "G" denotes guanosine (dGTP/rGTP) or an analogue thereof, "U" denotes uracil (rUTP) or an analogue thereof, and "T" denotes thymidine (dTTP) or an analogue thereof, unless otherwise noted. Usually oligonucleotides of the disclosure comprise the four natural nucleotides; however, they may also comprise non-natural nucleotide analogues.

A "probe" is an oligonucleotide that hybridizes specifically to a target nucleic acid sequence in a nucleic acid, preferably in an amplified nucleic acid, under conditions that promote hybridization, to form a detectable hybrid. Probe oligonucleotides comprise one or more of a contiguous nucleotide sequence, a target hybridizing sequence, a non-target hybridizing sequence, detectable labels, linkers, and nucleotide analogs. Probes preferably have oligonucleotide lengths from about 10 contiguous nucleotides up to 100 contiguous nucleotides. Certain specific probes that are preferred have target-hybridizing sequences in the length range of from 12-87, from 10-20, from 13-37, or from 17-23 nucleotides. A probe sequence may comprise RNA, DNA, analogs, and combinations thereof. The "backbone" of a probe may be made up of a variety of linkages known in the art, including one or more sugar-phosphodiester linkages, peptide-nucleic acid bonds (PNAs), phosphorothioate linkages, methylphosphonate linkages, or combinations thereof. Sugar moieties of the probe may be either ribose or deoxyribose, or similar compounds having known substitutions, such as, for example, 2'-O-methyl ribose and 2' halide substitutions (e.g., 2'-O-Me or 2'-F). The nucleotide analogues incorporated into a probe oligonucleotide sequence can include inosine or "I", 5-Me-dC, isoguanine, other derivatives of purine or pyrimidine bases, or abasic residues (e.g., nucleoside residues (e.g., The Biochemistry of the Nucleic Acids, pages 5-36, Adams, et al., ed., $11^{th}$ ed., 1992; PCT pub. no. WO 93/13121) The target nucleic acid sequence of a probe generally refers to a sequence contained within an amplified nucleic acid molecule that hybridizes specifically to at least a portion of the probe oligonucleotide using standard hydrogen bonding.

A probe may comprise target-specific sequences and optionally other sequences that are non-target hybridizing sequences (e.g., a sequence that does not hybridize the nucleic acid to be detected. Such non-target hybridizing sequences can include, for example, a promoter sequence, a restriction endonuclease recognition site, or sequences that contribute to three-dimensional conformation of the probe (e.g., see U.S. Pat. Nos. 5,118,801 and 5,312,728). Probes exhibiting at least some degree of self-complementarity include molecular torches and molecular beacons.

"Molecular Torches" can be designed to include distinct regions of self-complementarity (coined "the target hybridizing sequence domain" and "the target closing domain") that are connected by a joining region and which hybridize to one another under predetermined hybridization assay conditions. When exposed to denaturing conditions, the two complementary regions (which may be fully or partially complementary) of a molecular torch melt, leaving the target hybridizing sequence domain available for hybridization to a target nucleic acid sequence when the predetermined hybridization assay conditions are restored. Molecular torches are designed so that the target hybridizing sequence domain favors hybridization to the target nucleic acid sequence over the target closing domain. The target hybridizing sequence domain and the target closing domain of a molecular torch include interacting labels (e.g., fluorescent/quencher) positioned so that a different signal is produced when the molecular torch is self-hybridized as opposed to when the molecular torch is hybridized to a target nucleic acid sequence, thereby permitting detection of probe:target duplexes in a test sample in the presence of unhybridized probe having a viable label associated therewith. Molecular Torches are described, for example, in U.S. Pat. No. 6,361,945.

A "Molecular Beacon" can be designed to have a target hybridizing sequence, an affinity pair (or nucleic acid arms) holding the probe in a closed conformation in the absence of a target nucleic acid sequence, and a label pair that interacts when the probe is in a "closed" conformation. Hybridization of the target hybridizing sequence of the molecular beacon to its intended target nucleic acid sequence separates the members of the affinity pair, thereby shifting the probe to an "open" conformation. The shift to the "open" conformation is detectable due to reduced interaction of the label pair. Molecular Beacons are described, for example, in U.S. Pat. No. 5,925,517.

A probe optionally may contain a detectable label that either may be attached to the end of the probe or attached internally on the probe. The terms "label" or "detectable label" are used interchangeably herein and refer to one or more atoms that can be specifically detected to indicate the presence of a substance to which the one or more atoms is attached. A label can be a primary label that is directly detectable or secondary label that can be indirectly detected, for example, via direct or indirect interaction with a primary. A label can be linked to polynucleotide probes either directly or indirectly. Labels include dyes, particles, chromophores (e.g., an atom or molecule that imparts a detectable color), combinatorial fluorescence energy transfer labels, electrophores, redox active moieties (e.g., transition metals), enzymes, haptens, luminescent compounds (e.g., bioluminescent, phosphorescent, or chemiluminescent moieties), fluorophores, mass labels, and radiolabels. Labels and related detections methods are well known (see e.g., U.S. Pat. No. 6,627,748 (B1); Styer and Haugland, (1967), Proc. Natl. Acad. Sci. U.S.A. 98:719; U.S. Pat. Nos. 5,591,578; 5,491,063; 5,201,015)

The term "fluorophore" means a fluorescent chemical compound that can re-emit light upon light excitation. Fluorophores include, for example, fluorescent lanthanide complexes, including those of Europium and Terbium, fluorescein, rhodamine, tetramethylrhodamine, eosin, erythrosin, coumarin, methyl-coumarins, pyrene, Malacite green, Cy3, Cy5, CalFluor Red™, CalFluor Orange™, stilbene, Quasar dyes (e.g., Quasar 570, Quasar 670, Quasar 705), Lucifer Yellow, Cascade Blue™, Texas Red, Alexa dyes, phycoerythin, Bodipy, and others known in the art, see, e.g., Haugland, Molecular Probes Handbook (Eugene, OR), 6th Edition; The Synthegen catalog (Houston, Tex.); Lakowicz, Principles of Fluorescence Spectroscopy, 2nd Ed., Plenum Press New York (1999), and WO 98/59066.

The term "quencher" is used to refer to a molecule that absorbs light. Quenchers are commonly used in combination with a light emitting label such as a fluorophore to absorb emitted light when in close proximity to the fluorophore. Quenchers are well-known in the art and include, e.g., Black Hole Quencher™ (or BHQ™, BHQ-1™, or BHQ-2™), Blackberry Quencher, Dabcyl, QSY, and Tamra™ compounds, to name a few.

A "homogeneous detectable label" refers to a label that associates with a probe oligonucleotide and that can be detected without physically removing hybridized from unhybridized forms of the label or labeled probe. Examples of homogeneous labels have been described in detail in, for example, U.S. Pat. Nos. 5,283,174; 6,150,097; 5,201,015; 5,656,207; and 5,658,737.

Linear probes, molecular torches and beacons are preferably labeled with an interactive pair of detectable labels. Examples of detectable labels that are preferred as members of an interactive pair of detectable labels interact with each other by FRET or non-FRET energy transfer mechanisms. Fluorescence resonance energy transfer (FRET) involves the radiationless transmission of energy quanta from the site of absorption to the site of its utilization in the molecule, or system of molecules, by resonance interaction between chromophores, over distances considerably greater than interatomic distances, without conversion to thermal energy, and without the donor moiety and acceptor moiety coming into kinetic collision. The "donor" is the moiety that initially absorbs and then transfers the energy, and the "acceptor" is the moiety to which the energy is subsequently transferred. In addition to FRET, there are at least three other "non-FRET" energy transfer processes by which excitation energy can be transferred from a donor to an acceptor molecule.

When the two labels of a donor/acceptor pair are held sufficiently close that energy emitted by one label can be received or absorbed by the second label, whether by a FRET or non-FRET mechanism, the two labels are said to be in "energy transfer relationship" with each other. This is the case, for example, when a molecular beacon or molecular torch is maintained in the "closed" state by formation of a stem duplex, and fluorescent emission from a fluorophore attached to one arm of the probe is quenched by a quencher moiety on the opposite arm. This is also the case when, for example, a linear probe is labeled with a fluorophore and a quencher at a distance along the linear probe that fluorescent emission from the attached fluorophore is quenched by the attached quencher. In these instances, the spatial separation of the fluorophore and quencher molecules (e.g., by "opening" the molecular torch or beacon or by hydrolyzing the linear probe molecule).

Examples of donor/acceptor pairs, include fluorescein/tetramethylrhodamine, IAEDANS/fluororescein, EDANS/DABCYL, coumarin/DABCYL, fluorescein/fluorescein, BODIPY FL/BODIPY FL, fluorescein/DABCYL, lucifer yellow/DABCYL, BODIPY/DABCYL, eosine/DABCYL, erythrosine/DABCYL, tetramethylrhodamine/DABCYL, CalOrange/BHQ1, CalRed/BHQ2, FAM/BHQ1, Quasar/BHQ2, Texas Red/DABCYL, CY5/BH1, CY5/BH2, CY3/BH1, CY3/BH2 and fluorescein/QSY7 dye. Labels are available from LGC Biosearch Technologies (Petaluma, CA), Glen Research (Sterling, VA), Integrated DNA Technologies (Skokie, Il); Thermo Fisher (Waltham, MA), and others.

Synthetic techniques and methods of bonding labels to nucleic acids and detecting labels are well known in the art (e.g., see Sambrook, et al., Molecular Cloning, A Laboratory Manual, $2^{nd}$ ed. (Cold Spring Harbor Laboratory Press, Cold Spring Harbor, N.Y., 1989), Chapter 10; U.S. Pat. Nos. 5,658,737, 5,656,207, 5,547,842, 5,283,174, and 4,581,333, and published European Pat. App. No. 0 747 706). A probe may optionally contain a fluorophore and a quencher. The nucleotide residues of the probe that combine with the target nucleic acid sequence need not be strictly contiguous, as may be the case with a detectable moiety internal to the sequence of the probe.

An "amplification primer" or "primer" is an optionally modified oligonucleotide that hybridizes to a target nucleic acid sequence, or its complement, and can participate in a nucleic acid amplification reaction. Primer oligonucleotides comprise one or more of a contiguous nucleotide sequence, a target hybridizing sequence, a non-target hybridizing sequence, linkers, and nucleotide analogs. Primers preferably have oligonucleotide lengths from about 10 contiguous nucleotides up to 100 contiguous nucleotides. A primer sequence may comprise RNA, DNA, analogs, and combinations thereof. The "backbone" of a primer may be made up of a variety of linkages known in the art, including one or more sugar-phosphodiester linkages, peptide-nucleic acid bonds (PNAs), phosphorothioate linkages, methylphosphonate linkages, or combinations thereof. Sugar moieties of the primer may be either ribose or deoxyribose, or similar compounds having known substitutions, such as, for example, 2'-O-methyl ribose and 2' halide substitutions (e.g., 2'-O-Me or 2'-F). The nucleotide analogues incorporated into a primer oligonucleotide sequence can include inosine or "I", 5-Me-dC, isoguanine, other derivatives of purine or pyrimidine bases, or abasic residues (e.g., nucleoside residues. The target nucleic acid sequence of a primer generally refers to both a sequence contained within the genetic information of an organism to be detected and a sequence contained within an amplified nucleic acid molecule that hybridizes specifically to at least a portion of the primer oligonucleotide using standard hydrogen bonding. Primers hybridize to a target nucleic acid sequence and have a 3' end that can be extended by a DNA polymerase that incorporates nucleotides complementary to the target nucleic acid sequence to generate a double stranded portion thereof.

By "capture oligonucleotide" is meant at least one nucleic acid oligonucleotide that allows for joining of a target nucleic acid and an immobilized oligonucleotide due to base pair hybridization (preferably resulting in an immobilized probe:capture oligonucleotide:target nucleic acid complex). A capture oligonucleotide preferably includes two binding regions: a target nucleic acid-binding region and an immobilized probe-binding region, usually contiguous on the same oligonucleotide, although the capture oligonucleotide may include a target nucleic acid-binding region and an immobilized probe-binding region that are present on two different oligonucleotides joined together by one or more linkers. For example, an immobilized probe-binding region may be present on a first oligonucleotide, the target nucleic acid-binding region may be present on a second oligonucleotide, and the two different oligonucleotides are joined by hydrogen bonding with a linker that is a third oligonucleotide containing sequences that hybridize specifically to the sequences of the first and second oligonucleotides. The target hybridizing region of a capture probe can be specific for the target nucleic acid (e.g., sufficiently complementary to the target nucleic acid sequence) or non-specific for the target nucleic acid. One target capture system that includes a capture oligonucleotide is described in U.S. Pat. Nos. 6,110,678 & 9,051,601.

By "immobilized probe" or "immobilized nucleic acid" is meant a nucleic acid that joins, directly or indirectly, a capture oligonucleotide to an immobilized support. An immobilized probe is an oligonucleotide joined to a solid support that facilitates separation of bound target nucleic acids from unbound material in a sample.

The term "solid substrate" means any suitable medium present in the solid phase to which an antibody or an agent can be covalently or non-covalently affixed or immobilized.

By "separating" or "purifying" or "isolating" is meant that one or more components of the biological sample are removed from one or more other components of the sample. Sample components include nucleic acids in a generally aqueous solution phase that can also include other materials, for example, proteins, carbohydrates, lipids, and labeled probes. Preferably, the separating, isolating, or purifying step removes at least about 70%, more preferably at least about 90% and, even more preferably, at least about 95% of the other components present in the sample.

A "homogeneous assay" refers to a detection procedure that does not require physical separation of hybridized probe from non-hybridized probe prior to determining the extent of specific probe hybridization. Exemplary homogeneous assays can employ molecular beacons or other self-reporting probes that emit fluorescent signals when hybridized to an appropriate target nucleic acid sequences, chemiluminescent acridinium ester labels that can be selectively destroyed by chemical means unless present in a hybrid duplex, and other homogeneously detectable labels that will be familiar to those having an ordinary level of skill in the art.

"Amplification" refers to an in vitro procedure for obtaining multiple copies of a target nucleic acid sequence, its complement, or fragments thereof.

"Amplicon" refers to a DNA or RNA that is the product of a nucleic acid amplification or replication process. It can be formed using various methods, including polymerase chain reaction (PCR), ligase chain reaction (LCR), a transcription-associated amplification (e.g., TMA) etc.

The term "multiplex PCR" refers as a PCR reaction characterized in that two or more different amplification products, or amplicons, are generated by means of using two or more pairs of amplification primers in the same PCR reaction.

The term "multicolor" RT-PCR refers to a real time PCR assay characterized in that one or more different amplification products, or amplicons, generated either in a multiplex PCR or in a monoplex PCR (using only one pair of amplification primers) are (is) detected by using distinguishably labeled hybridization probes.

By "target nucleic acid" or "target" is meant a nucleic acid containing a target nucleic acid sequence. Described herein, target nucleic acids include Flu A nucleic acids, Flu B nucleic acids, RSV A nucleic acids and RSV B nucleic acids. By "target nucleic acid sequence", (also referred to as "target nucleotide sequence", "target sequence", "target region", "target nucleic acid molecule"), is meant a specific deoxyribonucleotide or ribonucleotide molecule or nucleotide sequence comprising all or part of the nucleotide sequence of a single-stranded nucleic acid molecule, and the deoxyribonucleotide or ribonucleotide sequence complementary thereto.

By "transcription associated amplification" is meant any type of nucleic acid amplification that uses an RNA polymerase to produce multiple RNA transcripts from a nucleic acid template. One example of a transcription associated amplification method, called "Transcription Mediated Amplification" (TMA), generally employs an RNA polymerase, a DNA polymerase, deoxyribonucleoside triphosphates, ribonucleoside triphosphates, and a promoter-template complementary oligonucleotide, and optionally may include one or more analogous oligonucleotides. Variations of TMA are well known in the art and are described, for example, in U.S. Pat. Nos. 5,437,990; 5,399,491; 5,554,516; 5,130,238; 4,868,105; and 5,124,246; published PCT application nos. WO 93/22461, WO 88/01302, WO 88/10315, WO 94/03472, and WO 95/03430.

SUMMARY

This disclosure provides compositions, including kits and reagents, and methods for in vitro diagnostic analysis of Influenza A Virus (Flu A), Influenza B Virus (Flu B), Respiratory Syncytial Virus type A (RSV A) or Respiratory Syncytial Virus type B (RSV B) nucleic acids in a sample. Preferably the in vitro diagnostic analysis utilizes polymerase chain reactions (PCR), though other in vitro assay methodologies are contemplated for use with the disclosed compositions. A particularly useful in vitro assay for use with the Flu A, Flu B, RSV A or RSV B target nucleic acids is a reverse transcription PCR assay, as these target nucleic acids are RNA viruses. Conveniently, in vitro amplification assays can performed simultaneously with in vitro detection assays (real-time PCR). Thus, a particularly useful and convenient in vitro assay for use with the Flu A, Flu B, RSV A or RSV B target nucleic acids is a real-time, reverse transcription PCR assay.

In one aspect, the sample is a biological sample. In one aspect the biological sample is a clinical sample. In another aspect the sample is a swab sample, for example, from nasopharyngeal (NP) swab specimens obtained from a patient. In some embodiments, the compositions and methods can be used to aid in the differential diagnosis of Flu A, Flu B, and RSV A and RSV B infections. Negative results do not preclude such infection. Conversely, positive results do not rule-out bacterial infections or co-infections with other viruses. The use of additional laboratory testing and clinical presentation may also be considered in order to obtain the final diagnosis of respiratory viral infection.

One aspect provides nucleic acid molecules that are hybridization assay probes useful for detecting Flu A, Flu B, RSV A, or RSV B target nucleic acid sequences. Preferably, such probe molecule species include a probe sequence that is substantially complementary to a probe target nucleic acid sequence in the viral genome, or an amplicon generated therefrom, being targeted for detection. In preferred embodiments, the probe target nucleic acid sequence consists of about 17 to about 100 contiguous bases contained within targeted viral genome (or amplicon generated therefrom). Preferably, a probe molecule is up to about 100 nucleotide residues in length, although lengths of between about 20-60 nucleotide residues are particularly preferred.

In the context of Flu A, in some preferred embodiments the probe comprises a sequence that is preferably SEQ NAME: FA1-F, SEQ NAME: FA1-G, SEQ NAME: FA1-H, SEQ NAME: FAM, SEQ NAME: FA1*-J, SEQ NAME: FA1*-K, SEQ NAME: FA1-L, SEQ NAME: FA1-M, SEQ NAME: FA1-N, SEQ NAME: FA1*-O, SEQ NAME: FA1*-P, or SEQ NAME: FA1*-Q. In other embodiments, the probe sequence is preferably SEQ NAME: FA2-R, SEQ NAME: FA2-S, SEQ NAME: FA2-T, SEQ NAME: FA2*-U, or SEQ NAME: FA2*-V (SEQ ID NOS:6 to 22). In particularly preferred embodiments, two probes, one from each of the foregoing groups, are used in tandem to target two different regions of the Flu A genome or amplification products generated therefrom.

In the context of Flu B, in preferred embodiments the probe sequence is preferably SEQ NAME: FB-B, SEQ NAME: FB-B!, SEQ NAME: FB-C, SEQ NAME: FB-C!, SEQ NAME: FB-D, SEQ NAME: FB-D!, SEQ NAME: FB-E, SEQ NAME: FB-E!, SEQ NAME: FB-F, SEQ NAME: FB-F!, SEQ NAME: FB-G, SEQ NAME: FB-G!, SEQ NAME: FB-H, SEQ NAME: FB-H!, SEQ NAME: FB-I, SEQ NAME: FB-I!, SEQ NAME: FB-J, SEQ NAME: FB-J!, SEQ NAME: FB-K, SEQ NAME: FB-K!, SEQ NAME: FB-L, SEQ NAME: FB-L!, SEQ NAME: FB-M, SEQ NAME: FB-M!, SEQ NAME: FB-N, SEQ NAME: FB-N!, SEQ NAME: FB-O, SEQ NAME: FB-O!, SEQ NAME: FB-Q, SEQ NAME: FB-R, SEQ NAME: FB-S, SEQ NAME: FB-T, SEQ NAME: FB-U, SEQ NAME: FB-V, SEQ NAME: FB*-W, or SEQ NAME: FB*-X (SEQ ID NOS:30 to 57 & 59 to 66).

In the context of RSV A, in preferred embodiments the probe sequence is preferably SEQ NAME: RA-A, SEQ NAME: RA-E, SEQ NAME: RA-F, SEQ NAME: RA-G, SEQ NAME: RA-H, SEQ NAME: RA-J, SEQ NAME: RA-J!, SEQ NAME: RA-K, SEQ NAME: RA-K!, SEQ NAME: RA-L, SEQ NAME: RA-L!, SEQ NAME: RA-M, SEQ NAME: RA-M!, SEQ NAME: RA-O, SEQ NAME: RA-P, SEQ NAME: RA-Q, SEQ NAME: RA*-W, and SEQ NAME: RA*-X (SEQ ID NOS:71, 75 to 78, 80 to 87, 89 to 91, 97 & 98).

In the context of RSV B, in preferred embodiments the probe sequence is preferably SEQ NAME: RB-D, SEQ NAME: RB-E, SEQ NAME: RB-V, SEQ NAME: RB-V!, SEQ NAME: RB-W, SEQ NAME: RB-W!, SEQ NAME: RB-X, SEQ NAME: RB-X!, SEQ NAME: RB-Y, and SEQ NAME: RB-Y! (SEQ ID NOS:102, 103, & 107 to 114).

Preferably, a probe molecule species is labeled, optionally distinguishably labeled such that any one probe molecule species can be distinguished from other probe molecule species in a multiplex detection assay. Distinguishable labeling can be achieved using two or more detectable labels, for example, a chemiluminescent moiety, a fluorophore moiety, and both a fluorophore moiety and a quencher moiety.

Another aspect the disclosure concerns nucleic acid molecules that are amplification primers engineered for use in in vitro amplification of target nucleic acid sequences. A related aspect of the disclosure relates to pairs of such primers that can be used to amplify desired amplicons that contain a target nucleic acid sequence. These primers include one or more of the following primers pairs: a first Flu A primer pair, a second Flu A primer pair that can be used to amplify a region of the Flu A target nucleic acid that is different from the region of the Flu A target nucleic acid that can be amplified using the first Flu A primer pair, a Flu B primer pair, an RSV A primer pair, and an RSV B primer pair. These primer pairs include first and second primers that can be used generate corresponding amplicons for Flu A, Flu B, RSV A, and/or RSV B if the viral pathogen is present in the biological sample being tested.

In general, a primer pair includes a first primer that includes a priming nucleotide sequence that is substantially complementary to a first target nucleic acid sequence of viral genome a portion of which is to be amplified. Preferably, the first and second target nucleic acid sequences are spaced apart in the target nucleic acid by at least 10, and preferably by about 50-1,000 nucleotides, and each of them preferably consists of about 17 to about 100 contiguous bases of the viral genome to be detected. In some embodiments, one or more of the primers in one or more primer pairs further comprises a primer upstream region having a nucleotide sequence that is not complementary to the primer's target nucleotide sequence.

Preferred first primers for generating a first Flu A amplicon have the priming nucleotide sequence of SEQ NAME: FA1-A or SEQ NAME: FA1-W. Preferred second primers useful with such first primers have the priming nucleotide sequence of SEQ NAME: FA1-Y or SEQ NAME: FA1-AB. SEQ ID NOS:1, 23, 25, & 28.

Preferred first primers for generating a second Flu A amplicon have the priming nucleotide sequence of SEQ NAME: FA2-B, SEQ NAME: FA2-C, SEQ NAME: FA2-D, SEQ NAME: FA2-E, or SEQ NAME: FA2-X. Preferred second primers useful with such first primers have the priming nucleotide sequence of SEQ NAME: FA2-Z or SEQ NAME: FA2-AA. SEQ ID NOS:2, 5, 24, 26, & 27.

Preferred first primers for generating a Flu B amplicon have the priming nucleotide sequence of SEQ NAME: FB-A or SEQ NAME: FB-Y. Preferred second primers useful with such first primers have the priming nucleotide sequence of SEQ NAME: FB-Z, SEQ NAME: FB-AA, and SEQ NAME: FB-AB. SEQ ID NOS:29 & 67 to 70.

Preferred first primers for generating an RSV A amplicon have the priming nucleotide sequence of SEQ NAME: RA-I or SEQ NAME: RA-N. Preferred second primers useful with such first primers have the priming nucleotide sequence of SEQ NAME: RA-B, SEQ NAME: RA-C, SEQ NAME: RA-D, SEQ NAME: RA-R, SEQ NAME: RA-S, SEQ NAME: RA-T, SEQ NAME: RA-U, and SEQ NAME: RA-V. SEQ ID NOS:79, 88, 72 to 74, & 92 to 96.

Preferred first primers for generating an RSV B amplicon have the priming nucleotide sequence of SEQ NAME: RB-A, SEQ NAME: RB-B, SEQ NAME: RB-C, and SEQ NAME: RB-U. Preferred second primers useful with such first primers have the priming nucleotide sequence of SEQ NAME: RB-F, SEQ NAME: RB-G, SEQ NAME: RB-U, and SEQ NAME: RB-Z. SEQ ID NOS:99 to 101, 104 to 106, & 115.

In some preferred embodiments, a probe and/or a primer contains one or more methylated cytosine bases.

Another related aspect of the disclosure concerns compositions that contain such probes, primers, and primer pairs. Such compositions include dry or liquid compositions. Dried compositions include lyophilized reagents containing one or more of a primer and a probe.

Another aspect of the disclosure relates to kits that include primers and/or probes. Such kits can also include salts, enzymes, dNTPs, dRTPs, other substrates, and/or instructions for use of such materials. The primers, probes, salts, enzymes, dNTPs, rNTPs, and/or other substrates of the kit may be in a dried form or in an aqueous form.

Another aspect of the disclosure relates to a reagent that contains primers and/or probes. Such reagents can also include salts, enzymes, dNTPs, rNTPs, and/or other substrates. The primers, probes, salts, enzymes, dNTPs, rNTPs, and/or other substrates of the reagents may be in a dried form or in an aqueous form.

Still another aspect of the disclosure concerns methods of using such primers and probes to analyze samples to determine if the sample contains one or more of a Flu A target nucleic acid, Flu B target nucleic acid, RSV A target nucleic acid, and RSV B target nucleic acid. The foregoing and other objects, features, and advantages of the compositions and methods will be apparent from the following detailed description and the claims.

DETAILED DESCRIPTION

Described herein are compositions, including kits and reagents, and methods for selectively detecting nucleic acids of various viral pathogens, specifically, Influenza A (Flu A), Influenza B (Flu B), Respiratory Syncytial Virus A (RSV A), and Respiratory Syncytial Virus B (RSV B), in a sample. These compositions and methods can be used, for example, in diagnostic applications, for screening clinical samples, nasopharyngeal samples, bronchoalveolar samples, donated blood and blood products or other tissues that may contain one or more of these pathogenic organisms.

As will be appreciated, any primer and probe sequences specific for Flu A, Flu B, RSV A, RSV B and/or other pathogenic viral target may be used as primers or probes in any suitable primer/probe-based in vitro nucleic acid amplification method adapted for amplification of an intended target nucleic acid. It is also understood that oligonucleotides having the sequences described herein could serve alternative functions in assays for detecting viral target nucleic acids. For example, a probe could be used as a primer (e.g., as one member of primer pair), and a primer could be used as a probe in an alternative detection assay.

The amplification primers are useful as components of uniplex or multiplex amplification reactions wherein amplicon species can be produced from target-specific primers in the reaction mixture. A multiplex amplification reaction includes primer pairs for amplifying two or more of Flu A, Flu B, RSV A, and RSV B, or, additionally includes primers for one or more of Flu A, Flu B, RSV A, and RSV B and one or more additional targets (e.g., human metapneumovirus, rhinovirus, adenovirus, parainfluenza virus, and/or bordetella).

Amplification methods useful in connection with the present disclosure include: Polymerase Chain Reaction (PCR); Transcription-Mediated Amplification (TMA); Nucleic Acid Sequence-Based Amplification (NASBA); Strand Displacement Amplification (SDA); and amplification methods using self-replicating polynucleotide molecules and replication enzymes such as MDV-1 RNA and Q-beta enzyme. Methods for carrying out these various amplification techniques respectively can be found in U.S. Pat. Nos. 4,965,188; 5,399,491; 5,455,166; and 5,472,840, published European patent application EP 0 525 882, and Lizardi, et al., BioTechnology 6:1197 (1988). In particularly preferred embodiments, Flu A, Flu B, RSV A, and RSV B nucleic acid sequences are amplified using real-time PCR (RT-PCR).

Due to the lack of sequence conservation among respiratory virus strains, particularly for Flu A, and to accommodate for mismatches/mutations between a primer or a probe and their corresponding target nucleic acid sequences in viral target nucleic acid, degenerate bases and non-Watson Crick (NWC) base pairing can, in some preferred embodiments, be included in a primer or probe oligonucleotide. A NWC position in an oligonucleotide refers to a position where the oligonucleotide is configured to hybridize to at least one target nucleic acid sequence with a non-Watson Crick pairing, such as G-U, G-T, or G-A (either the G or the U/T/A can be the base in the oligonucleotide). In some embodiments, the NWC position is configured to hybridize via a wobble (G-U or G-T) or purine-purine (G-A) pair. In some embodiments, when one or more degenerate bases have been identified in the target nucleic acid sequence for a single primer or probe, multiple primer species or probe species may be synthesized in order to include all base combinations.

Useful guidelines for designing amplification primers and probes with desired characteristics are known in the art, and are described herein. The optimal sites for amplifying and probing Flu A, Flu B, RSV A, and RSV B nucleic acids contain two, and preferably three, conserved regions each greater than about 15 bases in length, all spatially separated from one another within a region of about 1,000, preferably of about 500, and even more preferably, of about 200 bases of contiguous sequence of the target nucleic acid. The degree of amplification observed with a set of primers depends on several factors, including the ability of the primers to hybridize to their complementary sequences and their ability to be extended enzymatically. Because the extent and specificity of hybridization reactions are affected by a number of factors, manipulation of those factors will determine the exact sensitivity and specificity of a particular oligonucleotide, whether perfectly complementary to its target or not. The effects of varying assay conditions are known in the art, see, e.g., U.S. Pat. No. 5,840,488.

Amplification primers and probes should be positioned to minimize the stability of oligonucleotide:nontarget (e.g., nucleic acid with similar sequence to target nucleic acid) and oligonucleotide:oligonucleotide (e.g., primer dimers and self-complementarity) nucleic acid hybrids. It is preferred that the amplification primers and detection probes be able to distinguish between target and non-target sequences. In designing primers and probes, the differences in their melting temperature ($T_m$) values for oligonucleotide:target compared to oligonucleotide:non-target and oligonucleotide:oligonucleotide should be as large enough to favor oligonucleotide:target hybridizaztion. Also, long homopolymer tracts and high GC content are preferably avoided to reduce spurious primer extension.

As is known, nucleic acid hybridization involves the association of two single strands of complementary nucleic acid to form a hydrogen-bonded double strand. It is implicit that if one of the two strands is wholly or partially involved in a hybrid, then that strand will be less able to participate in formation of a new hybrid. By designing primers and probes so that substantial portions of the sequences of interest are single-stranded, the rate and extent of hybridization may be greatly increased. If the target is in a double-stranded form (as is the case with PCR products), denaturation prior to hybridization will typically be required.

Primers useful for conducting amplification reactions can have different lengths to accommodate the presence of extraneous sequences that do not participate in target binding, and that may not substantially affect amplification or detection procedures. For example, promoter-primers useful for performing amplification reactions in accordance with the disclosure have at least a minimal sequence that hybridizes to the desired target nucleic acid sequence, and a promoter sequence positioned upstream of that minimal sequence. However, insertion of sequences between the target binding sequence and the promoter sequence could change the length of the primer without compromising its utility in the amplification reaction. Additionally, the lengths of the amplification primers and detection probes are matters of choice as long as the sequences of these oligonucleotides conform to the minimal essential requirements for hybridizing with the desired complementary target sequence.

Hybridization assay probes useful for detecting Flu A, Flu B, RSV A, and RSV B nucleic acid sequences include a sequence of bases substantially complementary to the selected target nucleic acid sequence in the Flu A, Flu B, RSV A, or RSV B genome (or amplicon representing the corresponding region and its flanking or surrounding regions). Such probes may optionally have additional bases outside of the targeted nucleic acid region, which may or may not be complementary to Flu A, Flu B, RSV A, or RSV B nucleic acid.

Preferred probes are sufficiently homologous to the target nucleic acid to hybridize under stringent hybridization conditions corresponding to a designed amplification and detection reaction. For example, in PCR they extension and detection reactions are carried out such that an oligonucleotide would hybridize to its target nucleic acid sequence at a reaction temperature of about 60° C. Salt concentrations also impact hybridization of an oligonucleotide to its target nucleic acid sequence. An exemplary salt concentration is in a suitable range of about 0.6-0.9 M. Preferred salts include lithium chloride, but other salts such as sodium chloride and sodium citrate also can be used in the hybridization solution. Example high stringency hybridization conditions are also provided by 0.48 M sodium phosphate buffer, 0.1% sodium dodecyl sulfate, and 1 mM each of EDTA and EGTA, or by 0.6 M LiCl, 1% lithium lauryl sulfate, 60 mM lithium succinate and 10 mM each of EDTA and EGTA. Those skilled in the art are familiar with preparing solutions for nucleic acid hybridizations.

Probes in accordance with the disclosure have sequences complementary to, or corresponding to, a pre-selected target region of particular viral target nucleic acid targeted by the probe. Preferred probes have a probe sequence, which includes the target-hybridizing sequence of bases together with any base sequences that are not complementary to the nucleic acid that is to be detected, in the length range of from 10-100 nucleotides.

Amplification of nucleic acids by polymerase chain reaction (PCR) is a fundamental technique in molecular biology, typically requiring sample preparation, amplification, and product analysis. Although these steps are usually performed sequentially, amplification and analysis can occur simultaneously. DNA dyes or fluorescent probes can be added to the PCR mixture before amplification and used to analyze PCR products during amplification. Sample analysis occurs concurrently with amplification in the same tube within the same instrument. Such a combined approach decreases sample handling, saves time, and greatly reduces the risk of product contamination for subsequent reactions, as there is no need to remove the samples from their closed containers for further analysis. The concept of combining amplification with product analysis has become known as "real time" PCR (RT-PCR). See, for example, U.S. Pat. Nos. 6,174,670 and 8,137,616. In real time PCR, the formation of PCR products is monitored in each cycle of the PCR. The amplification is usually measured in thermocyclers that have additional devices for signal generation and detection from labels attached to probe oligonucleotide species during the amplification reaction. A number of such devices are known in the art for performing multiplex diagnostic assays with three, four, or more distinguishably labeled hybridization probes within one reaction vessel.

As is known, different formats exist for probe-based, real time detection of amplified DNA in multiplex assays. Common examples include "Taqman" probe systems, Molecular beacons and torches, single labeled probes, and FRET hybridization probes.

In TaqMan probe formats, a single-stranded hybridization probe for a given target is labeled with a donor/acceptor pair of detectable labels. When the donor (e.g., a fluorophore moiety) is excited with light of a suitable wavelength, the absorbed energy is transferred to the acceptor, (e.g., a quencher moiety), according to the principle of FRET. During the annealing step of a PCR reaction cycle, the hybridization probe binds to the target DNA and is degraded by the 5'-3' exonuclease activity of the Taq polymerase during the subsequent elongation phase. As a result, the excited donor moiety and the acceptor moiety become spatially separated, thus allowing for unquenched signal from the donor (e.g., a fluorescent emission) that is detected by the device. See, e.g., U.S. Pat. No. 5,538,848.

Molecular beacon and torch formats typically also include hybridization probes labeled with a donor/acceptor pair, with each of the donor moiety and the acceptor moiety being located at opposite ends of the probe. As a result of the secondary structure of the probe, which often involves hybridization of complementary regions at the ends of the probe, both the donor moiety and the acceptor moiety (e.g., the fluorescent moiety and the quencher moiety) are in spatial vicinity in solution. After hybridization of the probe's target hybridizing region to the desired target nucleic acid sequence, the donor moiety and the acceptor moiety are separated from one another such that after excitation of the donor moiety with light of a suitable wavelength its emission can be measured. See, e.g., U.S. Pat. No. 5,118,801.

In single label probe (SLP) formats, a single oligonucleotide is labeled with a single fluorescent dye at either the 5'- or 3'-end. Different designs can be used for oligonucleotide labeling, such as G-Quenching probes and Nitroindole-Dequenching probes. In G-Quenching embodiments, the fluorescent dye is attached via a C at the oligonucleotide's 5'- or 3'-end. Fluorescence decreases significantly when the probe is hybridized to the target if two G's are located on the target strand opposite to C and in position 1 aside of the complementary oligonucleotide probe. In the Nitroindole Dequenching embodiments, the fluorescent dye is attached to nitroindole at the 5'- or 3'-end of the oligonucleotide, and the itroindole decreases the fluorescent signaling from free (e.g., unhybridized) probe molecules. Fluorescence increases when the probe hybridizes to the target DNA due to a dequenching effect.

Multiplex assays that use FRET hybridization probes to detect target nucleic acids are particularly useful in homogenous hybridization assays (see, e.g., Matthews and Kricka, Analytical Biochemistry, vol. 169 (1988), pp: 1-25). In particular, the FRET hybridization probe format can be used in RT-PCR to detect amplified target DNA species.

Besides PCR and real time PCR, FRET hybridization probes can also be used for melting curve analysis. In such an assay, the target nucleic acid is amplified first in a typical PCR reaction with suitable amplification primers. The hybridization probes may already be present during the amplification reaction or added subsequently. After completion of the PCR reaction, the temperature of the sample is steadily increased, and fluorescence is detected as long as the hybridization probe is bound to the target DNA. At the melting temperature, the hybridization probe molecules are released from their complementary target sequences, and the fluorescent signal decreases immediately to the background level. This decrease is monitored with an appropriate fluorescence versus temperature-time plot such that a first derivative value can be determined, at which the maximum of fluorescence decrease is observed.

In some preferred embodiments, RT-PCR methods for amplifying and detecting multiple target DNA sequences in a multiplex assay are used. Such methods involve providing a composition or reaction mixture containing nucleic acids from biological sample, probes, primers, and a suitable polymerase activity to catalyze amplification, subjecting the reaction mixture to a thermocyling protocol such that amplification of the multiple target sequences occurs, and monitoring hybridization of each of the probe molecule species (e.g., pairs of FRET hybridization probes) at least once after a plurality of amplification cycles. In embodiments where the viral target nucleic acid(s) to be detected is/are comprised of one or more RNA molecules, such methods typically involve first converting RNA to DNA (e.g., a "complementary" DNA or "cDNA") through the use of a reverse polymerase activity.

In such multiplex embodiments, the composition or reaction mixture typically comprises at least 2, preferably 3-5, and most preferably 4 pairs of detection probes, preferably each pair of probes comprising a FRET donor moiety and a FRET acceptor moiety. In addition, such a composition or reaction mixture also comprises a number of reagents, including one or more of the following: buffers designed for PCR, dNTPs, a template dependent DNA polymerase (preferably a thermostable DNA polymerase), a reverse transcriptase.

During or after the amplification process is complete, the reaction is monitored to detect stable hybridization between one or more of the distinguishably labeled probe species present in the reaction and its corresponding target nucleic acid sequence (carried in an amplicon generated using the corresponding primer pair for the particular viral (or other) pathogen to be detected. Based on whether the donor moieties from each of the different donor/acceptor pairs are detected, it can then be determining if the biological sample contains Flu A, Flu B, RSV A, and/or RSV B and/or such other pathogens as are targeted in the particular assay.

Certain preferred kits will comprise one or more of a probe, a primer, a capture oligonucleotide, internal control oligonucleotides other ancillary oligonucleotides a buffer, dNTPs, DNA polymerase, reverse transcriptase, and instructions for using components of the kit (or a link to a website providing such instructions).

The following examples are provided to illustrate certain disclosed embodiments and are not to be construed as limiting the scope of this disclosure in any way.

General Reagents and Methods. Unless otherwise indicated, amplifications were performed using an ABI 7500 FAST® instrument. Viral isolates used as amplification targets or controls were diluted in suitable media, e.g., Micro Test M4 media (Remel Inc. Cat. No. R12500), Micro Test M5 Viral Transport Medium (Remel, Inc. Cat. No. R12515), Micro Test M6 Viral Transport Medium (Remel, Inc. Cat. No. R12530), Micro Test M4RT Viral Transport Medium (Remel, Inc. Cat. No. R12505), or Copan Universal Transport Medium (Copan Diagnostics, Inc., Cat. No. 330C). Nucleic acid was extracted from viral isolates using a non-specific target capture procedure as described in US Patent App. Pub. 2013/0209992.

PCR reaction mixtures were typically assembled as follows: 19.05 uL Supermix (Promega GoTaq® Supermix); 0.35 uL MMLV Reverse Transcriptase (35 U); 0.6 uL GoTaq MDX Hotstart Taq (3U); 5 uL of nucleic acids (primers, probe, and target in suitable diluent); =25 uL total reaction volume. Promega, Madison, WI; New England Biolabs, Ipswich, MA; Sigma-Aldrich, St. Louis MO; Thermo Fisher, Waltham, MA; and others.

Example 1

Multiplex RT-PCT Assay to Detect Flu A, Flu B, RSV A, and RSV B

This example describes a representative RT-PCR assay based on Taqman reagent chemistry to provide for the detection and differentiation of Influenza A Virus, Influenza B Virus, and Respiratory Syncytial Virus Types A and B in a biological sample.

Here, the process begins by collecting, for example, a nasopharyngeal swab specimen from a symptomatic human patient. Unless the sample is to be immediately assayed, the sample is preferably placed in sealable container (e.g., an RNase/DNase-free 1.5 mL polypropylene microcentrifuge tube) along with an appropriate volume of viral transport medium (VTM; e.g., Remel, Inc., Copan Diagnostics, Inc., or (Becton, Dickinson and Co.). Preferably, a Universal Internal Control (UIC) is also then added to the sample to monitor for inhibitors that may be present in the sample.

Next, nucleic acids in the sample are isolated, for example, by using a MagNA Pure LC System (Roche) and a MagNA Pure Total Nucleic Acid Isolation Kit (Roche; cat. no. 03038505001) or a NucliSENS easyMAG System (bioMérieux) and an Automated Magnetic Extraction Reagents (bioMérieux). Purified nucleic acids are then added to a reaction mix along with a thermostable DNA polymerase and a reverse transcriptase. The reaction mix contains oligonucleotide primer pairs and target-specific oligonucleotide probes for each of Flu A, Flu B, RSV A, and RSV B, as well as Taq DNA polymerase, buffer containing dNTPs (dATP, dCTP, dGTP, dTTP (or dUTP)), $MgCl_2$, and stabilizers, and bovine serum albumin. For reverse transcription of viral genomes, M-MLV Reverse Transcriptase can be used, and to protect RNA from degradation, an RNase inhibitor (e.g., RNase Inhibitor II) can also be included. Various control nucleic acids may also be included. Such controls may be, for example, non-infectious in vitro transcribed RNA of specific viral sequences and/or non-infectious plasmid DNA containing control sequences. If desired, two different sets of amplification primers and probes targeting different genomic regions of the viruses to be detected can be used for any given target genome, particularly when, as may be the case with Flu A, genetic variation between strains may be such that detection based on a single region may be insufficient to assure accurate analysis. The amplification primers of the various primer pairs are complementary to highly conserved regions of genetic sequences for these respiratory viruses. The probe species are each dual-labeled with a distinguishable reporter dye and a quencher.

Reverse transcription of RNA into cDNA and subsequent amplification of DNA may be performed, for example, on a Cepheid SmartCycler II instrument (Cepheid, Sunnyvale, CA). In this process, for each viral genome to be detected, the probe species for the target viral genome (or region thereof) anneals specifically to the target nucleotide sequence of the target nucleic acid molecule (e.g., a specific region of the Flu A genome), followed by primer extension and amplification. The Taqman reagent chemistry utilizes the 5'-3' exonuclease activity of the Taq polymerase to cleave the probe, thus separating the reporter dye from its quencher. This generates an increase in fluorescent signal upon excitation from a light source. With each cycle, additional reporter dye molecules are cleaved from their respective probes, further increasing the fluorescent signal. The amount of fluorescence at any given cycle is dependent on the number of amplification products (amplicons) present at that time. Fluorescence intensity is monitored during each PCR cycle by the real-time instrument.

Example 2

Amplification and Detection of Flu A, Flu B, RSV A & RSV B in Clinical Samples Remnant nasopharyngeal (NP) swab and lower and lower respiratory tract (LRT) specimens from individuals exhibiting signs and/or symptoms of a respiratory tract infection were analyzed in a multiplex real-time PCR assay using primers and probes for the amplification and detection of Flu A, Flu B, RSV A and RSV B target nucleic acids. NP swab and LRT samples were tested with the Panther Fusion Flu A/B/RSV assay.

For this example, 2930 remnant NP swab specimen were used. The specimen were processed to release nucleic acids. Briefly, remnant NP swab specimen were received in Remel transport media (Thermo Fisher, Waltham, MA). An aliquot of the transport media (500 ul) from each specimen was separately combined with a lysis reagent (710 ul) in a Panther Fusion Lysis Tube (Hologic, Marlborough, MA). Following an incubation, 360 ul of lysed specimen was combined with 450 ul of a target nucleic acid isolation reagent containing a capture oligonucleotide and a solid support. The target nucleic acid isolation reaction was performed on a Panther Fusion device (Hologic, Marlborough, MA), and as generally described in U.S. Pat. Nos. 6,110,678 & 9,051,601. Target nucleic acids isolated from each clinical specimen were then eluted from the capture reaction into a 50 ul eluate to provide 2930 sample conditions, each corresponding to one of the NP swab specimen. A nucleic acid amplification and detection reaction was set-up as follows: 5 ul from each sample condition was added to a well of a multiwall plate. Also contained within the well was 20 ul of a rehydrated real-time PCR reaction mixture. The dried PCR reaction mixture was rehydrated using 24 ul of a magnesium salt containing buffer. Components of this real-time PCR reaction mixture are described above and further comprised primers and probes with nucleotide sequences illustrated as SEQ ID NOS:5, 7, 12, 18, 23, 25 to 27, 64, 67, 68, 75, 79, 92, 101, 102, & 115. Probes for detecting Flu A amplification products were labeled with FAM/BHQ1, probes for detecting Flu B amplification products were labeled with CalRed/BHQ2, and probes for detecting RSV A and RSV B amplification products were labeled with CalOrange/BHQ1 (labels available from LGC Biosearch Technologies, Petaluma, CA). Each sample condition was independently added to a PCR reaction microtube. Control wells included an internal control, a positive control and a negative control.

Each PCR reaction microtube was then placed on a Panther Fusion device (Hologic, Inc., Marlborough, MA) and analyzed for the presence or absence of one or more of the target nucleic acids in each well. Of the 2930 NP swab specimen, 61 provided inconsistent results, and thus were deemed invalid and excluded from the evaluation results; 189/2869 (6.6%) were positive for Flu A target nucleic acid; 55/2869 (1.9%) were positive for Flu B target nucleic acid; and 365/2869 (12.7%) were positive for RSV A and/or RSV B.

A similar assay was performed using the remnant lower respiratory tract (LRT) specimen, with the exception that 250 ul of the LRT specimen was combined with 250 ul of lysis reagent, and then 360 ul of this combined solution was used for the target nucleic acid reaction. For this example, 144 remnant LRT specimen were used. The specimen were treated (specimen lysis, nucleic acid isolation, amplification, and detection) as is generally described above in this example. Of the 144 LRT specimen, 4 provided inconsistent results or were not tested, and thus were deemed invalid and excluded from the evaluation results; 3/140 (2.1%) were positive for Flu A target nucleic acid; 0/140 (0.0%) were positive for Flu B target nucleic acid; and 1/140 (0.7%) were positive for RSV A and/or RSV B.

These results show that the assay is a sensitive and specific assay for the detection of target nucleic acids from NP swab specimen. These results also show that the assay is sensitive for the detection of Flu A target nucleic acids, but on these LRT specimen sensitivity could not be determined for Flu B and RSV A & B target nucleic acids. These results show that the assay has high specificity for Flu A, Flu B, RSV A and RSV B target nucleic acids.

Example 3

Exemplary Oligonucleotide Sequences

Table 1 illustrates a number of primer and probe sequences that are useful as compositions, in kits, as diagnostic reagents, and/or in methods for the amplification or detection of one or more of Flu A, Flu B, RSV-A, and RSV-B. The following Table 1 illustrates only the nucleotide sequences. It is understood that these sequences may further include detectable labels, sugar modifications (e.g., 2'-methoxy), base modifications (e.g., a methylated base), and other chemical components that are not represented in the illustrated contiguous arrangements of symbols.

TABLE 1

| SEQ ID NO: | SEQ Name: | Sequence* | Oligo-nucleo-tide Type |
|---|---|---|---|
| SEQ ID NO: 1 | FA1-A | GATCTTGAGGCTCTCATG | Primer |
| SEQ ID NO: 2 | FA2-B | ATAACRTTCCATGGRGCCAA | Primer |
| SEQ ID NO: 3 | FA2-C | ATAACRTTCCATGGGGCCAA | Primer |
| SEQ ID NO: 4 | FA2-D | ATAACGTTCCATGGRGCCA | Primer |
| SEQ ID NO: 5 | FA2-E | ATAACGTTCCATGGGGCCAA | Primer |
| SEQ ID NO: 6 | FA1-F | CCCTTAGTCAGAGGTGACAG | Probe |
| SEQ ID NO: 7 | FA1-G | TCAGGCCCCCTCAAAGCCGAGATCGCC | Probe |
| SEQ ID NO: 8 | FA1-H | TCAGGCCCCCTCAAAGCCGARATCGC | Probe |
| SEQ ID NO: 9 | FA1-I | TCAGGCCCCCTCAAAGCCGAGATCGC | Probe |
| SEQ ID NO: 10 | FA1*-J | 3'-AGUCCGGGGGAGUUUCGGCTUUAGCG-5' | Probe |
| SEQ ID NO: 11 | FA1*-K | 3'-AGUCCGGGGGAGUUUCGGCTCUAGCG-5' | Probe |
| SEQ ID NO: 12 | FA1-L | AGCCAUTCCATGAGAGCCTCAAGATCC | Probe |
| SEQ ID NO: 13 | FA1-M | AGCCAYTCCATRAGAGCCTCAAGATC | Probe |

TABLE 1-continued

| SEQ ID NO: | SEQ Name: | Sequence* | Oligo-nucleo-tide Type |
|---|---|---|---|
| SEQ ID NO: 14 | FA1-N | AGCCA**U**TCCAT**G**AGAGCCTCAAGATC | Probe |
| SEQ ID NO: 15 | FA1*-O | 3′-UCGGU**G**AGGUA**C**UCUCGGAGUUCUAG-5′ | Probe |
| SEQ ID NO: 16 | FA1*-P | 3′-UCGGU**A**AGGUA**C**UCUCGGAGUUCUAG-5′ | Probe |
| SEQ ID NO: 17 | FA1*-Q | 3′-UCGGU**A**AGGUA**U**UCUCGGAGUUCUAG-5′ | Probe |
| SEQ ID NO: 18 | FA2-R | CTGGTGCACTTGCCAGTTGUATGC | Probe |
| SEQ ID NO: 19 | FA2-S | CTGGTGCACTTGCCAGTTC**Y**ATG | Probe |
| SEQ ID NO: 20 | FA2-T | CTGGTGCACTTGCCAGTTC**U**ATG | Probe |
| SEQ ID NO: 21 | FA2*-U | 3′-GACCACGUGAACGGUCAAG**A**UAC-5′ | Probe |
| SEQ ID NO: 22 | FA2*-V | 3′-GACCACGUGAACGGUCAAG**G**UAC-5′ | Probe |
| SEQ ID NO: 23 | FA1-W | CTTCTAACCGAGGTCGAAACGT | Primer |
| SEQ ID NO: 24 | FA2-X | ATAACGTTCCATGGGGCCAA | Primer |
| SEQ ID NO: 25 | FA1-Y | CCCTTAGTCAGAGGTGACA | Primer |
| SEQ ID NO: 26 | FA2-Z | CCCATTCTGTTGTATATGAG | Primer |
| SEQ ID NO: 27 | FA2-AA | CCCATCCTGTTGTATATGAG | Primer |
| SEQ ID NO: 28 | FA1-AB | GGTGAGCGTGAACACAAA | Primer |
| SEQ ID NO: 29 | FB-A | AGTGGAGGATGAAGAAGATGGC | Primer |
| SEQ ID NO: 30 | FB-B! | GCCTGCTTTGCCTTCTCCATCTTCTGTGCAGGC | Torch |
| SEQ ID NO: 31 | FB-B | GCCTGCTTTGCCTTCTCCATCTTCTG | Probe |
| SEQ ID NO: 32 | FB-C! | GCCTGCTTTGCCTTCTCCATCTTCTGTAGCAGGC | Torch |
| SEQ ID NO: 33 | FB-C | GCCTGCTTTGCCTTCTCCATCTTCTGT | Probe |
| SEQ ID NO: 34 | FB-D! | GCGCTAGTTCTGCTTTGCCTTCTCCATCTTCCTAGCGC | Torch |
| SEQ ID NO: 35 | FB-D | GCGCTAGTTCTGCTTTGCCTTCTCCATCTTC | Probe |
| SEQ ID NO: 36 | FB-E! | GCGCTAGTTCTGCTTTGCCTTCTCCATCTTCCTAGCGC | Torch |
| SEQ ID NO: 37 | FB-E | GCGCTAGTTCTGCTTTGCCTTCTCCATCTTC | Probe |
| SEQ ID NO: 38 | FB-F! | GCGCTAGTTCTGCTTTGCCTTCTCCATCTTCCTAGCGC | Torch |
| SEQ ID NO: 39 | FB-F | GCGCTAGTTCTGCTTTGCCTTCTCCATCTTC | Probe |
| SEQ ID NO: 40 | FB-G! | GCTGCTAGTTCTGCTTTGCCTTCTCCATCGCAGC | Torch |
| SEQ ID NO: 41 | FB-G | GCTGCTAGTTCTGCTTTGCCTTCTCCATC | Probe |
| SEQ ID NO: 42 | FB-H! | GCCTGCTAGTTCTGCTTTGCCTTCTCCATCGCAGGC | Torch |
| SEQ ID NO: 43 | FB-H | GCCTGCTAGTTCTGCTTTGCCTTCTCCATC | Probe |
| SEQ ID NO: 44 | FB-I! | GCCTGCTAGTTCTGCTTTGCCTTCTCCATCGCAGGC | Torch |
| SEQ ID NO: 45 | FB-I | GCCTGCTAGTTCTGCTTTGCCTTCTCCATC | Probe |
| SEQ ID NO: 46 | FB-J! | GCCTGCTAGTTCTGCTTTGCCTTCTCCATCAGCAGGC | Torch |
| SEQ ID NO: 47 | FB-J | GCCTGCTAGTTCTGCTTTGCCTTCTCCATC | Probe |
| SEQ ID NO: 48 | FB-K! | GCCTGCTAGTTCTGCTTTGCCTTCTCCATCAGCAGGC | Torch |
| SEQ ID NO: 49 | FB-K | GCCTGCTAGTTCTGCTTTGCCTTCTCCATC | Probe |
| SEQ ID NO: 50 | FB-L! | GCCTGCTAGTTCTGCTTTGCCTTCTCCATCAGCAGGC | Torch |

TABLE 1-continued

| SEQ ID NO: | SEQ Name: | Sequence* | Oligo-nucleo-tide Type |
|---|---|---|---|
| SEQ ID NO: 51 | FB-L | GCCTGCTAGTTCTGCTTTGCCTTCTCCATC | Probe |
| SEQ ID NO: 52 | FB-M! | GCCTGCTAGTTCTGCTTTGCCTTCTCCATCTAGCAGGC | Torch |
| SEQ ID NO: 53 | FB-M | GCCTGCTAGTTCTGCTTTGCCTTCTCCATC | Probe |
| SEQ ID NO: 54 | FB-N! | GCGGAGAAGGCAAAGCAGAAUTAGCAGTCTCCGC | Torch |
| SEQ ID NO: 55 | FB-N | GCGGAGAAGGCAAAGCAGAAUTAGCAG | Probe |
| SEQ ID NO: 56 | FB-O! | GCGGAGAAGGCAAAGCAGAAUTAGCAGTCTCCGC | Torch |
| SEQ ID NO: 57 | FB-O | GCGGAGAAGGCAAAGCAGAAUTAGCAG | Probe |
| SEQ ID NO: 58 | FB-P | TCTTTCCCACCRAACCAACA | Primer |
| SEQ ID NO: 59 | FB-Q | CTAGTTCTGCTTTGCCTTCTCCATCTTCT | Probe |
| SEQ ID NO: 60 | FB-R | AAGACTCCCACCGCAGTTTCAGCT | Probe |
| SEQ ID NO: 61 | FB-S | AAGACTCCCACCGCAGTTTCAGCT | Probe |
| SEQ ID NO: 62 | FB-T | AAGACTCCCACCGCAGTTTCAGCT | Probe |
| SEQ ID NO: 63 | FB-U | CTA**R**TTCTGCTTTGCCTTCTCCATCTTCT | Probe |
| SEQ ID NO: 64 | FB-V | CTA**G**TTCTGCTTTGCCTTCTCCATCTTCT | Probe |
| SEQ ID NO: 65 | FB*-W | 3′-GAU**U**AAGACGAAACGGAAGAGGUAGAAGA-5′ | Probe |
| SEQ ID NO: 66 | FB*-X | 3′-GAU**C**AAGACGAAACGGAAGAGGUAGAAGA-5′ | Probe |
| SEQ ID NO: 67 | FB-Y | GAGACACAATTGCCTACCTGCTT | Primer |
| SEQ ID NO: 68 | FB-Z | GAGTCTAGGTCAAAUTCTTTCCCACC | Primer |
| SEQ ID NO: 69 | FB-AA | GGTGCTCTTGACCAAATTGGG | Primer |
| SEQ ID NO: 70 | FB-AB | CTTTCCCACCRAACCAACAGTG | Primer |
| SEQ ID NO: 71 | RA-A | TTAGTCATYACAGTGACTGACAACAAAGG | Probe |
| SEQ ID NO: 72 | RA-B | AGGTAAGCTCCWAGATCTACTAT | Primer |
| SEQ ID NO: 73 | RA-C | AGGTAAGCTCCWAGATCTACTAT | Primer |
| SEQ ID NO: 74 | RA-D | AGGTAAGCTCCTAGATCTACTAT | Primer |
| SEQ ID NO: 75 | RA-E | TTAGTCATUACAGTGACTGACAACAAAGGAGC | Probe |
| SEQ ID NO: 76 | RA-F | TAGACCATGTGAATTCCCTGC | Probe |
| SEQ ID NO: 77 | RA-G | TTAGTCAT**Y**ACAGTGACTGACAACAAAGG | Probe |
| SEQ ID NO: 78 | RA-H | TTAGTCAT**U**ACAGTGACTGACAACAAAGG | Probe |
| SEQ ID NO: 79 | RA-I | ACAAATGCAAAAATCATACCTTACTC | Primer |
| SEQ ID NO: 80 | RA-J! | CGTGGCTTTATGTATTTGAATGCTCCTTTGGCCACG | Torch |
| SEQ ID NO: 81 | RA-J | CGTGGCTTTATGTATTTGAATGCTCCTTTG | Probe |
| SEQ ID NO: 82 | RA-K! | CGTGGCTTTATGTATTTGAATGCTCCTTTGGCCACG | Torch |
| SEQ ID NO: 83 | RA-K | CGTGGCTTTATGTATTTGAATGCTCCTTTG | Probe |
| SEQ ID NO: 84 | RA-L! | CGGTGGCTTTATGTATTTGAATGCTCCTTTGGCCACCG | Torch |
| SEQ ID NO: 85 | RA-L | CGGTGGCTTTATGTATTTGAATGCTCCTTTG | Probe |
| SEQ ID NO: 86 | RA-M! | CGGTGGCTTTATGTATTTGAATGCTCCTTTGAGCCACC G | Torch |

TABLE 1-continued

| SEQ ID NO: | SEQ Name: | Sequence* | Oligo-nucleo-tide Type |
|---|---|---|---|
| SEQ ID NO: 87 | RA-M | CGGTGGCTTTATGTATTTGAATGCTCCTTTG | Probe |
| SEQ ID NO: 88 | RA-N | ACAAATGCAAAAATCATACCTTACTC | Primer |
| SEQ ID NO: 89 | RA-O | TTAGTCATTACAGTGACTGACAACAAAGG | Probe |
| SEQ ID NO: 90 | RA-P | TTAGTCATYACAGTGACTGACAACAAAGG | Probe |
| SEQ ID NO: 91 | RA-Q | TTAGTCATUACAGTGACTGACAACAAAGG | Probe |
| SEQ ID NO: 92 | RA-R | AGGTAAGCTCCGAGATCTACTAT | Primer |
| SEQ ID NO: 93 | RA-S | CTAGGTAAGCTCCAAGATCTACTAT | Primer |
| SEQ ID NO: 94 | RA-T | CTAGGTAAGCTCCAAGATCTACTAT | Primer |
| SEQ ID NO: 95 | RA-U | CTAGGTAAGCTCCTAGATCTACTAT | Primer |
| SEQ ID NO: 96 | RA-V | CTAGGTAAGCTCCTAGATCTACTAT | Primer |
| SEQ ID NO: 97 | RA*-W | 3′-AAUCAGUA**G**UGUCACUGACUGUUGUUUCC-5′ | Probe |
| SEQ ID NO: 98 | RA*-X | 3′-AAUCAGUA**A**UGUCACUGACUGUUGUUUCC-5′ | Probe |
| SEQ ID NO: 99 | RB-A | TGAAGTTGATGAACAAAGTGG | Primer |
| SEQ ID NO: 100 | RB-B | GATGATGATCCYGCATCACTAAC | Primer |
| SEQ ID NO: 101 | RB-C | GATGATGATCCUGCATCACTAAC | Primer |
| SEQ ID NO: 102 | RB-D | ATGGGTGCCTATGTTCCAGTCATCTG | Probe |
| SEQ ID NO: 103 | RB-E | CACCAGCCCTCAATACCACCC | Probe |
| SEQ ID NO: 104 | RB-F | GCTTCAATGGTCCACAGTT | Primer |
| SEQ ID NO: 105 | RB-G | GCTTCAATGGTCCACAGTT | Primer |
| SEQ ID NO: 106 | RB-U | GATGATGATCCUGCATCACTAAC | Primer |
| SEQ ID NO: 107 | RB-V! | CGCTGCTGGCACAGATGACTGGAACATAGCAGCG | Torch |
| SEQ ID NO: 108 | RB-V | CGCTGCTGGCACAGATGACTGGAACATA | Probe |
| SEQ ID NO: 109 | RB-W! | CCGAGCAAGTCTGCTGGCACAGATGACTGGGCTCGG | Torch |
| SEQ ID NO: 110 | RB-W | CCGAGCAAGTCTGCTGGCACAGATGACTGG | Probe |
| SEQ ID NO: 111 | RB-X! | CCGAGCAAGTCTGCTGGCACAGATGACTGGTTGCTCGG | Torch |
| SEQ ID NO: 112 | RB-X | CCGAGCAAGTCTGCTGGCACAGATGACTGG | Probe |
| SEQ ID NO: 113 | RB-Y! | CGCCAGTCATCTGTGCCAGCAGACTTGCTGGCG | Torch |
| SEQ ID NO: 114 | RB-Y | CGCCAGTCATCTGTGCCAGCAGACTTG | Probe |
| SEQ ID NO: 115 | RB-Z | TAGTATGTTGATGCTTGCAAGTTC | Primer |

TABLE 1-continued

| SEQ ID NO: | SEQ Name: | Sequence* | Oligo-nucleo-tide Type |
|---|---|---|---|
| SEQ ID NO: 116 | Flu A | GenBank Accession No. KC355801.1 (13-JAN-13) | Target |
| SEQ ID NO: 117 | Flu B | GenBank Accession No. JX266956.1 (22-OCT-12) | Target |
| SEQ ID NO: 118 | RSV-A | GenBank Accession No. AY911262.1 (5-JUL-5) | Target |
| SEQ ID NO: 119 | RSV-B | GenBank Accession No. AF013254.1 (2-NOV-97 with non-sequence changes on 30-SEP-99) | Target |

*All sequences are written in the 5' to 3' orientation unless indicated otherwise.
Sequence symbols are per Table 1 of World Intellectual Property Organization (WIPO) Handbook on Industrial Property Information and Documentation, Standard ST.25 (1998) ("WIPO ST.25 (1998)").
Sequence Names containing "!" are molecular torch probes.
Bold/underline on a symbol indicates degenerate or non-Watson/Crick residue relative to target.

All of the articles, devices, systems, and methods disclosed and claimed herein can be made and executed without undue experimentation in light of the present disclosure. While the devices, systems, and methods of this disclosure have been described in terms of preferred embodiments, it will be apparent to those of skill in the art that variations may be applied to the articles and methods without departing from the spirit and scope of the disclosure. All such variations and equivalents apparent to those skilled in the art, whether now existing or later developed, are deemed to be within the spirit and scope of the disclosure. It will also be appreciated that computer-based embodiments of the instant disclosure can be implemented using any suitable hardware and software.

All patents, patent applications, and publications mentioned in the specification are indicative of the levels of those of ordinary skill in the art to which the disclosure pertains. All patents, patent applications, and publications are herein incorporated by reference in their entirety for all purposes and to the same extent as if each individual publication was specifically and individually indicated to be incorporated by reference in its entirety for any and all purposes.

What is claimed is:

1. A method for the determining the presence or absence of a Flu A target nucleic acid in a sample, the method comprising the steps of:

(A) contacting the sample with;

(a) a first Flu A primer combination comprising a first Flu A primer and a second Flu A primer, wherein:

(i) the first Flu A primer comprises a target hybridizing sequence consisting of the nucleic acid sequence of SEQ ID NO:23; and (ii) the second Flu A primer comprises a target hybridizing sequence consisting of the nucleotide sequence of SEQ ID NO:25; and (b) a second Flu A primer combination comprising a third Flu A primer, a fourth Flu A primer, and a fifth Flu A primer, wherein:

(i) the third Flu A primer comprises a target hybridizing sequence consisting of the nucleotide sequence of SEQ ID NO:24; and (ii) the fourth Flu A primer comprises a target hybridizing sequence consisting of the nucleotide sequence of SEQ ID NO:26 and the fifth Flu A primer comprises a target hybridizing sequence consisting of the nucleotide sequence of SEQ ID NO:27;

(B) performing an in vitro nucleic acid amplification reaction wherein the Flu A target nucleic acid, if present, is amplified by the first Flu A primer combination to generate a first Flu A amplification product and/or the second Flu A primer combination to generate a second Flu A amplification product; and (C) detecting the presence or absence of the first Flu A amplification product and/or the second Flu A amplification product;

wherein detecting the presence of the first Flu A amplification product and/or the second Flu A amplification product indicates the presence of the Flu A target nucleic acid in the sample.

2. The method of claim 1, wherein one or more of the first Flu A primer, the second Flu A primer, the third Flu A primer, and the fourth Flu A primers further comprises a primer upstream region having a nucleotide sequence that is not complementary to the Flu A target nucleic acid.

3. The method of claim 1, wherein the detecting step (C) is performed using a first Flu A probe and a second Flu A probe wherein (i) the first Flu A probe comprises a sequence that is complementary to a sequence in the first Flu A amplification product, is 20 to 100 contiguous bases in length, and comprises a nucleotide sequence selected from the group consisting of: SEQ ID NO:9, SEQ ID NO:14, SEQ ID NO:6, SEQ ID NO:7, SEQ ID NO:8, SEQ ID NO:10, SEQ ID NO:11, SEQ ID NO:12, SEQ ID NO:13, SEQ ID NO:15, SEQ ID NO:16, and SEQ ID NO:17; and (ii) the second Flu A probe comprises a sequence that is complementary to a sequence in the second Flu A amplification product sequence, is 23 to 100 contiguous bases in length, and comprises a nucleotide sequence selected from the group consisting of: SEQ ID NO:18, SEQ ID NO:19, SEQ ID NO:20, SEQ ID NO:21, and SEQ ID NO:22;

wherein each probe is detectably labeled.

4. The method of claim 3, wherein the first Flu A probe and the second Flu A probe are each detectably labeled with a donor/acceptor label pair.

5. The method of claim 3, wherein the first Flu A probe and the second Flu A probe are each detectably labeled with the same label or distinguishable labels.

6. The method of claim 3, wherein the first Flu A probe and the second Flu A probe are independently labeled with one or more detectable labels selected from the group consisting: of a chemiluminescent moiety, a fluorophore moiety, a quencher moiety, and both a fluorophore moiety and a quencher moiety.

7. The method of claim 6, the first Flu A probe and the second Flu A probe are labeled with fluorescein and a quencher moiety.

8. The method of claim 3, wherein at least one primer and/or at least one probe contains one or more methylated cytosine bases.

9. The method of claim 1, wherein the sample comprises a clinical specimen, a nasopharyngeal specimen, a broncho-alveolar specimen, or a lower respiratory tract specimen.

* * * * *

SEQUENCE LISTING

<160> NUMBER OF SEQ ID NOS: 119

<210> SEQ ID NO 1
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 1
gatcttgagg ctctcatg 18

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide -continued

<400> SEQUENCE: 2
ataacrttcc atggrgccaa 20

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 3
ataacrttcc atggggccaa 20

<210> SEQ ID NO 4
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 4
ataacgttcc atggrgcca 19

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 5
ataacgttcc atggggccaa 20

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 6
cccttagtca gaggtgacag 20

<210> SEQ ID NO 7
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 7
tcaggccccc tcaaagccga gatcgcc 27

<210> SEQ ID NO 8
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 8
tcaggccccc tcaaagccga ratcgc 26

<210> SEQ ID NO 9

-continued

<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 9
tcaggccccc tcaaagccga gatcgc 26

<210> SEQ ID NO 10
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 10
gcgauutcgg cuuugagggg gccuga 26

<210> SEQ ID NO 11
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 11
gcgauctcgg cuuugagggg gccuga 26

<210> SEQ ID NO 12
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 12
agccautcca tgagagcctc aagatcc 27

<210> SEQ ID NO 13
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 13
agccaytcca tragagcctc aagatc 26

<210> SEQ ID NO 14
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 14
agccautcca tgagagcctc aagatc 26

<210> SEQ ID NO 15
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 15

-continued gaucuugagg cucucaugga guggcu 26

<210> SEQ ID NO 16
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 16
gaucuugagg cucucaugga auggcu 26

<210> SEQ ID NO 17
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 17
gaucuugagg cucuuaugga auggcu 26

<210> SEQ ID NO 18
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 18
ctggtgcact tgccagttgu atgc 24

<210> SEQ ID NO 19
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 19
ctggtgcact tgccagttcy atg 23

<210> SEQ ID NO 20
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 20
ctggtgcact tgccagttcu atg 23

<210> SEQ ID NO 21
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 21
cauagaacug gcaagugcac cag 23

<210> SEQ ID NO 22
<211> LENGTH: 23
<212> TYPE: DNA

-continued

<213> ORGANISM: Artificial Sequence
<220> FEATURE:
<223> OTHER INFORMATION: Synthetic Oligonucleotide

<400> SEQUENCE: 22
cauggaacug gcaagugcac cag 23

<210> SEQ ID NO 23
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 23
cttctaaccg aggtcgaaac gt 22

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 24
ataacgttcc atggggccaa 20

<210> SEQ ID NO 25
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 25
cccttagtca gaggtgaca 19

<210> SEQ ID NO 26
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 26
cccattctgt tgtatatgag 20

<210> SEQ ID NO 27
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 27
cccatcctgt tgtatatgag 20

<210> SEQ ID NO 28
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 28
ggtgagcgtg aacacaaa 18

<210> SEQ ID NO 29
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 29
agtggaggat gaagaagatg gc 22

<210> SEQ ID NO 30
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 30
gcctgctttg ccttctccat cttctgtgca ggc 33

<210> SEQ ID NO 31
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 31
gcctgctttg ccttctccat cttctg 26

<210> SEQ ID NO 32
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 32
gcctgctttg ccttctccat cttctgtagc aggc 34

<210> SEQ ID NO 33
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 33
gcctgctttg ccttctccat cttctgt 27

<210> SEQ ID NO 34
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 34
gcgctagttc tgctttgcct tctccatctt cctagcgc 38

<210> SEQ ID NO 35
<211> LENGTH: 31
<212> TYPE: DNA
<213> ORGANISM: Artificial Sequence
<220> FEATURE:

<223> OTHER INFORMATION: Synthetic Oligonucleotide

<400> SEQUENCE: 35
gcgctagttc tgctttgcct tctccatctt c 31

<210> SEQ ID NO 36
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 36
gcgctagttc tgctttgcct tctccatctt cctagcgc 38

<210> SEQ ID NO 37
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 37
gcgctagttc tgctttgcct tctccatctt c 31

<210> SEQ ID NO 38
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 38
gcgctagttc tgctttgcct tctccatctt cctagcgc 38

<210> SEQ ID NO 39
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 39
gcgctagttc tgctttgcct tctccatctt c 31

<210> SEQ ID NO 40
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 40
gctgctagtt ctgctttgcc ttctccatcg cagc 34

<210> SEQ ID NO 41
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 41
gctgctagtt ctgctttgcc ttctccatc 29

-continued

<210> SEQ ID NO 42
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 42
gcctgctagt tctgctttgc cttctccatc gcaggc 36

<210> SEQ ID NO 43
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 43
gcctgctagt tctgctttgc cttctccatc 30

<210> SEQ ID NO 44
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 44
gcctgctagt tctgctttgc cttctccatc gcaggc 36

<210> SEQ ID NO 45
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 45
gcctgctagt tctgctttgc cttctccatc 30

<210> SEQ ID NO 46
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 46
gcctgctagt tctgctttgc cttctccatc agcaggc 37

<210> SEQ ID NO 47
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 47
gcctgctagt tctgctttgc cttctccatc 30

<210> SEQ ID NO 48
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 48
gcctgctagt tctgctttgc cttctccatc agcaggc 37

<210> SEQ ID NO 49
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 49
gcctgctagt tctgctttgc cttctccatc 30

<210> SEQ ID NO 50
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 50
gcctgctagt tctgctttgc cttctccatc agcaggc 37

<210> SEQ ID NO 51
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 51
gcctgctagt tctgctttgc cttctccatc 30

<210> SEQ ID NO 52
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 52
gcctgctagt tctgctttgc cttctccatc tagcaggc 38

<210> SEQ ID NO 53
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 53
gcctgctagt tctgctttgc cttctccatc 30

<210> SEQ ID NO 54
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 54
gcggagaagg caaagcagaa utagcagtct ccgc 34

<210> SEQ ID NO 55
<211> LENGTH: 27

<212> TYPE: DNA
<213> ORGANISM: Artificial Sequence
<220> FEATURE:
<223> OTHER INFORMATION: Synthetic Oligonucleotide

<400> SEQUENCE: 55
gcggagaagg caaagcagaa utagcag 27

<210> SEQ ID NO 56
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 56
gcggagaagg caaagcagaa utagcagtct ccgc 34

<210> SEQ ID NO 57
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 57
gcggagaagg caaagcagaa utagcag 27

<210> SEQ ID NO 58
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 58
tctttcccac craaccaaca 20

<210> SEQ ID NO 59
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 59
ctagttctgc tttgccttct ccatcttct 29

<210> SEQ ID NO 60
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 60
aagactccca ccgcagtttc agct 24

<210> SEQ ID NO 61
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 61
aagactccca ccgcagtttc agct 24

<210> SEQ ID NO 62
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 62
aagactccca ccgcagtttc agct 24

<210> SEQ ID NO 63
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 63
ctarttctgc tttgccttct ccatcttct 29

<210> SEQ ID NO 64
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 64
ctagttctgc tttgccttct ccatcttct 29

<210> SEQ ID NO 65
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 65
agaagaugga gaaggcaaag cagaauuag 29

<210> SEQ ID NO 66
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 66
agaagaugga gaaggcaaag cagaacuag 29

<210> SEQ ID NO 67
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 67
gagacacaat tgcctacctg ctt 23

<210> SEQ ID NO 68
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 68
gagtctaggt caaautcttt cccacc 26

<210> SEQ ID NO 69
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 69
ggtgctcttg accaaattgg g 21

<210> SEQ ID NO 70
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 70
ctttcccacc raaccaacag tg 22

<210> SEQ ID NO 71
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 71
ttagtcatya cagtgactga caacaaagg 29

<210> SEQ ID NO 72
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 72
aggtaagctc cwagatctac tat 23

<210> SEQ ID NO 73
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 73
aggtaagctc cwagatctac tat 23

<210> SEQ ID NO 74
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 74
aggtaagctc ctagatctac tat 23

<210> SEQ ID NO 75
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 75
ttagtcatua cagtgactga caacaaagga gc 32

<210> SEQ ID NO 76
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 76
tagaccatgt gaattccctg c 21

<210> SEQ ID NO 77
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 77
ttagtcatya cagtgactga caacaaagg 29

<210> SEQ ID NO 78
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 78
ttagtcatua cagtgactga caacaaagg 29

<210> SEQ ID NO 79
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 79
acaaatgcaa aaatcatacc ttactc 26

<210> SEQ ID NO 80
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 80
cgtggcttta tgtatttgaa tgctcctttg gccacg 36

<210> SEQ ID NO 81
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 81
cgtggcttta tgtatttgaa tgctcctttg 30

<210> SEQ ID NO 82
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 82
cgtggcttta tgtatttgaa tgctcctttg gccacg 36

<210> SEQ ID NO 83
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 83
cgtggcttta tgtatttgaa tgctcctttg 30

<210> SEQ ID NO 84
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 84
cggtggcttt atgtatttga atgctccttt ggccaccg 38

<210> SEQ ID NO 85
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 85
cggtggcttt atgtatttga atgctccttt g 31

<210> SEQ ID NO 86
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 86
cggtggcttt atgtatttga atgctccttt gagccaccg 39

<210> SEQ ID NO 87
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 87
cggtggcttt atgtatttga atgctccttt g 31

<210> SEQ ID NO 88

<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 88
acaaatgcaa aaatcatacc ttactc 26

<210> SEQ ID NO 89
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 89
ttagtcatta cagtgactga caacaaagg 29

<210> SEQ ID NO 90
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 90
ttagtcatya cagtgactga caacaaagg 29

<210> SEQ ID NO 91
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 91
ttagtcatua cagtgactga caacaaagg 29

<210> SEQ ID NO 92
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 92
aggtaagctc cgagatctac tat 23

<210> SEQ ID NO 93
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 93
ctaggtaagc tccaagatct actat 25

<210> SEQ ID NO 94
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 94
ctaggtaagc tccaagatct actat 25

<210> SEQ ID NO 95
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 95
ctaggtaagc tcctagatct actat 25

<210> SEQ ID NO 96
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 96
ctaggtaagc tcctagatct actat 25

<210> SEQ ID NO 97
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 97
ccuuuguugu cagucacugu gaugacuaa 29

<210> SEQ ID NO 98
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 98
ccuuuguugu cagucacugu aaugacuaa 29

<210> SEQ ID NO 99
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 99
tgaagttgat gaacaaagtg g 21

<210> SEQ ID NO 100
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 100
gatgatgatc cygcatcact aac 23

<210> SEQ ID NO 101
<211> LENGTH: 23
<212> TYPE: DNA

<213> ORGANISM: Artificial Sequence
<220> FEATURE:
<223> OTHER INFORMATION: Synthetic Oligonucleotide

<400> SEQUENCE: 101
gatgatgatc cugcatcact aac 23

<210> SEQ ID NO 102
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 102
atgggtgcct atgttccagt catctg 26

<210> SEQ ID NO 103
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 103
caccagccct caataccacc c 21

<210> SEQ ID NO 104
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 104
gcttcaatgg tccacagtt 19

<210> SEQ ID NO 105
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 105
gcttcaatgg tccacagtt 19

<210> SEQ ID NO 106
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 106
gatgatgatc cugcatcact aac 23

<210> SEQ ID NO 107
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 107
cgctgctggc acagatgact ggaacatagc agcg 34

<210> SEQ ID NO 108
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 108
cgctgctggc acagatgact ggaacata 28

<210> SEQ ID NO 109
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 109
ccgagcaagt ctgctggcac agatgactgg gctcgg 36

<210> SEQ ID NO 110
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 110
ccgagcaagt ctgctggcac agatgactgg 30

<210> SEQ ID NO 111
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 111
ccgagcaagt ctgctggcac agatgactgg ttgctcgg 38

<210> SEQ ID NO 112
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 112
ccgagcaagt ctgctggcac agatgactgg 30

<210> SEQ ID NO 113
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 113
cgccagtcat ctgtgccagc agacttgctg gcg 33

<210> SEQ ID NO 114
<211> LENGTH: 27
<212> TYPE: DNA
<213> ORGANISM: Artificial Sequence
<220> FEATURE:

<223> OTHER INFORMATION: Synthetic Oligonucleotide

<400> SEQUENCE: 114
cgccagtcat ctgtgccagc agacttg 27

<210> SEQ ID NO 115
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 115
tagtatgttg atgcttgcaa gttc 24

<210> SEQ ID NO 116
<211> LENGTH: 984
<212> TYPE: DNA
<213> ORGANISM: Influenza A virus
<300> PUBLICATION INFORMATION:
<308> DATABASE ACCESSION NUMBER: KC355801.1
<309> DATABASE ENTRY DATE: 2013-01-13
<313> RELEVANT RESIDUES IN SEQ ID NO: (1)..(984)

<400> SEQUENCE: 116
atgagtcttc taaccgaggt cgaaacgtac gttctttcta tcataccgtc aggccccctc 60
aaagccgaga tcgcgcagag actggaaagt gtctttgcag gaaagaacac agatcttgag 120
gctctcatgg aatggctaaa gacaagacca atcttgtcac ctctgactaa gggaatttta 180
ggatttgtgt tcacgctcac cgtgcccagt gagcgaggac tgcagcgtag acgctttgtc 240
caaaatgccc tgaatgggaa tggggaccca aacaacatgg atagagcagt taaactatac 300
aagaagctca aaagagaaat aacgttccat ggggccaagg aggtgtcact aagctattca 360
actggtgcac ttgccagttg catgggcctc atatacaaca ggatgggaac agtgaccaca 420
gaagctgctt ttggtctagt gtgtgccact tgtgaacaga ttgctgattc acagcatcgg 480
tctcacagac agatggctac aaccaccaat ccactaatca ggcatgagaa cagaatggtg 540
ctggctagca ctacggcaaa ggctatggaa cagatggctg gatcgagtga acaggcagcg 600
gaggccatgg aggttgctaa tcagactagg cagatggtac atgcaatgag aactattggg 660
actcatccta gctccagtac gggtctgaaa gatgaccttc ttgaaaattt gcaggcctac 720
cagaagcgaa tgggagtgca gatgcagcga ttcaagtgat cttctcgcca ttgcagcaaa 780
tatcattggg atcttgcacc tgatattgtg gattactgat cgtctttttt tcaaatgtat 840
ttatcgtcgc tttaaatacg gtttgaaaag agggccttct acggaaggag ggcctgagtc 900
catgagggaa gaatatcaac aggaacagca gagtgctgtg gatgttgacg atggtcattt 960
tgtcaacata gagctagagt aaaa 984

<210> SEQ ID NO 117
<211> LENGTH: 1076
<212> TYPE: DNA
<213> ORGANISM: Influenza B virus
<300> PUBLICATION INFORMATION:
<308> DATABASE ACCESSION NUMBER: JX266956.1
<309> DATABASE ENTRY DATE: 2012-10-22
<313> RELEVANT RESIDUES IN SEQ ID NO: (1)..(1076)

<400> SEQUENCE: 117
atgtcgctgt ttggagacac aattgcctac ctgctttcat tgacagaaga tggagaaggc 60
aaagcagaac tagcagaaaa attacactgt tggttcggtg ggaaagaatt tgacctagac 120

-continued

```
tctgccttgg aatggataaa aaacaaaaga tgcttaactg atatacagaa agcactaatt    180

ggtgcatcta tctgcttttt aaaacccaaa gaccaggaaa gaaaaagaag attcatcaca    240

gagcccctat caggaatggg aacaacagca acaaaaaaga agggcctgat tctagctgag    300

agaaaaatga gaaaatgtgt gagcttccat gaagcatttg aaatagcaga aggccatgaa    360

agctcagcgt tactgtattg tctcatggtc atgtacctga atcctggaaa ttattcaatg    420

caagtaaaac taggaacgct ctgtgctttg tgcgagaaac aagcatcaca ttcacacagg    480

gctcatagca gagcagcgag atcttcagtg cccggagtga gacgagaaat gcagatggtc    540

tcagctatga acacagcaaa aacaatgaat ggaatgggaa aaggagaaga cgtccaaaaa    600

ctggcagaag aactgcaaag caacattgga gtattgagat ctctgggggc aagccaaaag    660

aatggggaag gaattgcaaa ggatgtaatg gaagtgctaa agcagagctc tatgggaaat    720

tcagctcttg tgaagaaata cctataatgc tcgaaccatt tcagattctt tcaatttgtt    780

cttttatttt atcagctctc catttcatgg cctggacaat aggacatttg aatcaaataa    840

aaagaggagt aaacatgaaa atacgaataa aggggccaaa taaagagacg ataaacagag    900

aggtatcaat tttgagacac aattaccaaa aagaaattca ggctaaagaa gcaatgaagg    960

aagtactctc tgacaacatg gaggtattga gtgaccacat agtaattgag gggctttctg   1020

cagaagagat aataaaaatg ggtgaaacag ttttggaggt agaaaaatcg cattaa       1076
```

<210> SEQ ID NO 118
<211> LENGTH: 15226
<212> TYPE: DNA
<213> ORGANISM: respiratory syncytial virus
<300> PUBLICATION INFORMATION:
<308> DATABASE ACCESSION NUMBER: AY911262.1
<309> DATABASE ENTRY DATE: 2005-07-05
<313> RELEVANT RESIDUES IN SEQ ID NO: (1)..(15226)

<400> SEQUENCE: 118

```
acgcgaaaaa atgcgtacaa caaacttgcg taaaccaaaa aaatggggca aataagaatt     60

tgataagtac cacttaaatt taactccctt ggttagagat gggcagcaat tcgttgagta    120

tgataaaagt tagattacaa aatttgtttg acaatgatga agtagcattg ttaaaaataa    180

catgctatac tgacaaatta atacatttaa ctaatgcttt ggctaaggca gtgatacata    240

caatcaaatt gaatggcatt gtgtttgtgc atgttattac aagtagtgat atttgcccta    300

ataataatat tgtagtaaaa tccaatttca caacaatgcc agtgctacaa aatggaggtt    360

atatatggga aatgatggaa ttaacacatt gctctcaacc taatggtcta atagatgaca    420

attgtgaaat taaattctcc aaaaaactaa gtgattcaac aatgaccaat tatatgaatc    480

aattatctga attacttgga tttgatctta atccataaat tataattaat atcaactagc    540

aaatcaatgt cactagcacc attagttaat ataaaactta acagaagaca aaaatggggc    600

aaataaatca actcagccaa cccaaccatg gacacaaccc acaatgatac cacaccacaa    660

agactgatga tcacagacat gagaccgttg tcacttgaga ctacaataac atcactaacc    720

agagacatca taacacacag atttatatac ttaataaatc atgaatgcat agtgagaaaa    780

cttgatgaaa gacaggccac atttacattc ctggtcaact atgaaatgaa actattgcac    840

aaagtaggaa gcactaaata taaaaaatat actgaataca acacaaaata tggcactttc    900

cctatgccga tattcatcaa tcatgatggg ttcttagaat gcattggcat taagcctaca    960

aagcatactc ccataatata caagtatgat ctcaatccat gaatttcaac acaagattca   1020
```

-continued cacaatccaa aacaacaact ttatgcataa ctacactcca tagtccaaat ggagcctgaa 1080
aattatagta atttaaaatt aaggagagac ataagataga agatggggca aatacaaaga 1140
tggctcttag caaagtcaag ttgaatgata cactcaacaa agatcaactt ctgtcatcta 1200
gcaaatacac catccaacgg agcacaggag atagtattga tactcctaat tatgatgtgc 1260
agaaacacat caataagtta tgtggcatgt tattaatcac agaagatgct aatcataaat 1320
tcactgggtt aataggtatg ttatatgcta tgtctaggtt aggaagagaa gacaccataa 1380
aaatactcag agatgcggga tatcatgtaa aagcaaatgg agtagatgta acaacacatc 1440
gtcaagacat caatgggaaa gaaatgaaat ttgaagtgtt aacattggca agcttaacaa 1500
ctgaaattca aatcaacatt gagatagaat ctagaaaatc ctacaaaaaa atgctaaaag 1560
aaatgggaga ggtagctcca gaatacaggc atgattctcc tgattgtggg atgataatat 1620
tatgtatagc agcattagta ataaccaaat tggcagcagg ggatagatct ggtcttacag 1680
ccgtgattag gagagctaat aatgtcctaa aaaatgaaat gaaacgttac aaaggcttac 1740
tacccaagga tatagccaac agcttctatg aagtgtttga aaaacatccc cactttatag 1800
atgtttttgt tcattttggt atagcacaat cttccaccag aggtggcagt agagttgaag 1860
ggatttttgc aggattgttt atgaatgcct atggtgcagg gcaagtaatg ctacggtggg 1920
gagtcttagc aaaatcagtt aaaaatatta tgttaggaca tgctagtgtg caagcagaaa 1980
tggaacaagt tgttgaggtt tatgaatatg cccaaaaatt gggtggagaa gcaggattct 2040
accatatatt gaacaaccca aaagcatcat tattatcttt gactcaattt cctcactttt 2100
ccagtgtagt attaggcaat gctgctggcc taggcataat gggagagtac agaggtacac 2160
cgaggaatca agatctatat gatgcagcaa aggcatatgc tgaacaactc aaagaaaatg 2220
gtgtgattaa ctacagtgta ttagacttga cagcagaaga actagaggct atcaaacatc 2280
agcttaatcc aaaagataat gatgtagagc tttgagttaa taaaaaatgg ggcaaataaa 2340
tcatcatgga aaagtttgct cctgaattcc atggagaaga tgcaaacaac agggctacta 2400
aattcctaga atcaataaag ggcaaattca catcacctaa agatcccaag aaaaaagata 2460
gtatcatatc tgtcaactca atagatatag aagtaaccaa agaaagccct ataacatcaa 2520
attcaaccat tattaaccca acaaatgaga cagatgataa tgcagggaac aagcccaatt 2580
atcaaagaaa acctctagta agtttcaaag aagaccctat accaagtgat aatccctttt 2640
caaaactata caaagaaacc atagagacat ttgataacaa tgaagaagaa tctagctatt 2700
catatgaaga aataaatgat cagacgaacg ataatataac tgcaagatta gataggattg 2760
atgaaaaatt aagtgaaata ctaggaatgc ttcacacatt agtagtagca agtgcaggac 2820
ctacatctgc tagggatggt ataagagatg ccatggttgg tttaagagaa gaaatgatag 2880
aaaaaatcag aactgaagca ttaatgacca atgacagatt agaagctatg gcaagactca 2940
ggaatgagga aagtgaaaag atggcaaaag acacatcaga tgaagtgtct ctcaatccaa 3000
catcagagaa attgaacaac ctgttggaag ggaatgatag tgacaatgat ctatcacttg 3060
aagatttctg attagttaca aatctgcact tcaacacaca acaccaacag aagaccaaca 3120
aacaaaccaa cccactcatc caaccaaaca tccatccgcc aatcagccaa acagccaaca 3180
aaacaaccag ccaatccaaa accagccacc tggaaaaaat cgacaatata gttacaaaaa 3240
aagaaaaggg tggggcaaat atggaaacat acgtgaacaa gcttcacgaa ggctccacat 3300
acacagctgc tgttcaatac aatgtcctag aaaaagacga tgaccctgca tcacttacaa 3360
tatgggtgcc catgttccaa tcatctatgc cagcagattt acttataaaa gaactagcta 3420
atgtcaacat actagtgaaa caaatatcca cacccaaggg accttcacta agagtcatga 3480
taaactcaag aagtgcattg ctagcacaaa tgcccagcaa atttaccata tgtgctaatg 3540
tgtccttgga tgaaagaagc aaactggcat atgatgtaac cacaccctgt gaaatcaagg 3600
catgtagtct aacatgccta aaatcaaaaa atatgttaac tacagttaaa gatctcacta 3660
tgaagacact caaccccaca catgatatta ttgctttatg tgaatttgaa aacatagtaa 3720
catcaaaaaa agtcataata ccaacatacc taagatccat cagtgtcaga aataaagatc 3780
tgaacacact tgaaaatata acaaccactg aattcaaaaa tgccatcaca aatgcaaaaa 3840
tcatccctta ctcaggatta ctattagtca tcacagtgac tgacaacaaa ggagcattca 3900
aatacataaa gccgcaaagt caattcatag tagatcttgg agcttaccta gaaaaagaaa 3960
gtatatatta tgttaccaca aattggaagc acacagctac acgatttgca atcaaaccca 4020
tggaagatta accttttttcc tccacatcag tgagtcaatt catacaaact ttctacctac 4080
attcttcact tcaccattac aatcacaaac actctgtggt tcaaccaatc aaacaaaact 4140
tatctgaagt ctcagatcat cccaagtcat tgttcatcag atctagtaat caaataagtt 4200
aataaaaata tacacatggg gcaaataatc atcggaggaa atccaactaa tcacaatatc 4260
tgttaacata gacaagtcaa cacaccagac agaatcaacc aatggaaaat acatccataa 4320
caatagaatt ctcaagcaaa ttctggcctt actttacact aatacacatg atcacaacaa 4380
taatctcttt gctaatcata atctccatca tgactgcaat actaaacaaa ctttgtgaat 4440
ataacgtatt ccataacaaa acctttgagt taccaagagc tcgagtcaac acatagcatt 4500
catcaatcta atagctcaaa atagtaacct tgcatttaaa agtgaacaac ccccacctct 4560
ttacaacacc tcattaacat cccaccatgc aaaccaccat ccatactata aagtagttaa 4620
ttaaaaatag tcataacaat gaactaggat atcaagacta acaataacgt tggggcaaat 4680
gcaaacatgt ccaaaaacaa ggaccaacgc accgctaaga cactagaaaa gacctgggac 4740
actctcaatc atttattatt catatcatcg ggcttatata agttaaatct taaatctata 4800
gcacaaatca cattatccat tctggcaatg ataatctcaa cttcacttat aattacagcc 4860
atcatattca tagcctcggc aaaccacaaa gtcacactaa caactgcaat catacaagat 4920
gcaacaagcc agatcaagaa cacaacccca acatacctca ctcaggatcc tcagcttgga 4980
atcagcttct ccaatctgtc tgaaattaca tcacaaacca ccaccatact agcttcaaca 5040
acaccaggag tcaagtcaaa cctgcaaccc acaacagtca agactaaaaa cacaacaaca 5100
acccaaacac aacccagcaa gcccactaca aaacaacgcc aaaacaaacc accaaacaaa 5160
cccaataatg attttcactt cgaagtgttt aactttgtac cctgcagcat atgcagcaac 5220
aatccaacct gctgggctat ctgcaaaaga ataccaaaca aaaaaccagg aaagaaaacc 5280
accaccaagc ctacaaaaaa accaaccttc aagacaacca aaaaagatct caaacctcaa 5340
accactaaac caaaggaagt acccaccacc aagcccacag aagagccaac catcaacacc 5400
accaaaacaa acatcacaac tacactgctc accaacaaca ccacaggaaa tccaaaactc 5460
acaagtcaaa tggaaacctt ccactcaacc tcctccgaag gcaatctaag cccttctcaa 5520
gtctccacaa catccgagca cccatcacaa ccctcatctc cacccaacac aacacgccag 5580
tagttattaa aaaacatatt atcacaaaag gccatgacca actcaaacag aatcaaaata 5640
aactctgggg caaataacaa tggagttgcc aatcctcaaa gcaaatgcaa ttaccacaat 5700
cctcgctgca gtcacatttt gctttgcttc tagtcaaaac atcactgaag aattttatca 5760

-continued

```
atcaacatgc agtgcagtta gcaaaggcta tcttagtgct ctaagaactg gttggtatac   5820
tagtgttata actatagaat taagtaatat caaggaaaat aagtgtaatg gaacagatgc   5880
taaggtaaaa ttgataaacc aagaattaga taaatataaa aatgctgtaa cagaattgca   5940
gttgctcatg caaagcacaa cagcagcaaa caatcgagcc agaagagaac taccaaggtt   6000
tatgaattat acactcaaca ataccaaaaa aaccaatgta acattaagca agaaaaggaa   6060
aagaagattt cttggttttt tgttaggtgt tggatctgca atcgccagtg gcattgctgt   6120
atctaaggtc ctgcacttag aaggagaagt gaacaagatc aaaagtgctc tactatccac   6180
aaacaaggcc gtagtcagct tatcaaatgg agttagtgtc ttaaccagca aagtgttaga   6240
cctcaaaaac tatatagata aacaattgtt acctattgtg aataagcaaa gctgcagaat   6300
atcaaatata gaaactgtga tagagttcca acaaaagaac aacagactac tagagattac   6360
cagggaattt agtgttaatg caggtgtaac tacacctgta agcacttaca tgttaactaa   6420
tagtgaatta ttgtcattaa tcaatgatat gcctataaca aatgatcaga aaaagttaat   6480
gtccaacaat gttcaaatag ttagacagca aagttactct atcatgtcca taataaaaga   6540
ggaagtctta gcatatgtag tacaattacc actatatggt gtgatagata caccttgttg   6600
gaaattacac acatcccctc tatgtacaac caacacaaaa gaagggtcaa acatctgttt   6660
aacaagaact gacagaggat ggtactgtga caatgcagga tcagtatctt tcttcccaca   6720
agctgaaaca tgtaaagttc aatcgaatcg agtattttgt gacacaatga acagtttaac   6780
attaccaagt gaagtaaatc tctgcaatgt tgacatattc aatcccaaat atgattgtaa   6840
aattatgact tcaaaaacag atgtaagcag ctccgttatc acatctctag gagccattgt   6900
gtcatgctat ggcaaaacta aatgtacagc atccaataaa aatcgtggaa tcataaagac   6960
attttctaac gggtgtgatt atgtatcaaa taaaggggtg gacactgtgt ctgtaggtaa   7020
cacattatat tatgtaaata agcaagaagg caaaagtctc tatgtaaaag gtgaaccaat   7080
aataaatttc tatgacccat tagtattccc ctctgatgaa tttgatgcat caatatctca   7140
agtcaatgag aagattaacc agagtttagc atttattcgt aaatccgatg aattattaca   7200
tcatgtaaat gctggtaaat caaccacaaa tatcatgata actactataa ttatagtgat   7260
tatagtaata ttgttatcat taattgctgt tggactgctc ctatactgta aggccagaag   7320
cacaccagtc acactaagca aggatcaact gagtggtata aataatattg catttagtaa   7380
ctgaataaaa atagcaccta atcatgttct tacaatggtt tactatctgc tcatagacaa   7440
cccatctatc attggatttt cttaaaatct gaacttcatc gaaactctta tctataaacc   7500
atctcactta cactatttaa gtagattcct agtttatagt tatataaaac acaattgaat   7560
accagattaa cttactatct gtaaaaatga gaactggggc aaatatgtca cgaaggaatc   7620
cttgcaaatt tgaaattcga ggtcattgct tgaatggtaa gagatgtcat tttagtcata   7680
attattttga atggccaccc catgcactgc tcgtaagaca aaactttatg ttaaacagaa   7740
tacttaagtc tatggataaa agtatagata ccttatcaga aataagtgga gctgcagagt   7800
tggacagaac agaagagtat gctcttggtg tagttggagt gctagagagt tatataggat   7860
caataaataa tataactaaa caatcagcat gtgttgccat gagcaaactc ctcactgaac   7920
tcaatagtga tgatatcaaa aaactgagag acaatgaaga gctaaattca cccaagataa   7980
gagtgtacaa tactgtcata tcatatattg aaagcaacag gaaaaacaat aaacaaacta   8040
tccatctgtt aaaaagattg ccagcagacg tattgaagaa aaccatcaaa aacacattgg   8100
atatccacaa gagcataacc atcaacaacc caaaagaatt aactgttagt gatacaaatg   8160
```

-continued

```
accatgccaa aaataatgat actacctgac aaatatcctt gtagtataac ttccatacta   8220
ataacaagta gatgtagagt cactatgtat aatcgaaaga acacactata tttcaatcaa   8280
aacaacccaa ataaccatat gtactcaccg aatcaaacat tcaatgaaat ccattggacc   8340
tcacaagact tgattgacac aattcaaaat tttctacagc atctaggtgt tattgaggat   8400
atatatacaa tatatatatt agtgtcataa cactcaatcc taatactgac catatcgttg   8460
aattattaat tcaaataatt caagctgtgg gacaaaatgg atcccattat taatggaaat   8520
tctgctaatg tttatctaac cgatagttat ttaaaaggtg ttatctcttt ctcagagtgt   8580
aatgctttag gaagttacat attcaatggt ccttatctca aaaatgatta taccaactta   8640
attagtagac aaaatccatt aatagaacac atgaatctaa agaaactaaa tataacacag   8700
tccttaatat ctaagtatca taaaggtgaa ataaaattag aagagcctac ttattttcag   8760
tcattactta tgacatacaa gagtatgacc tcgttggaac agattgctac cactaattta   8820
cttaaaaaga taataagaag agctatagaa ataagtgatg tcaaagtcta tgctatattg   8880
aataaactag ggcttaaaga aaaggacaag attaaatcca acaatggaca ggatgaagac   8940
aactcagtta ttacgaccat aatcaaagat gatatacttt cagctgttaa ggataatcaa   9000
tctcatctta aagcagacaa aaatcactct acaaaacaaa aagacacaat caaaacaaca   9060
ctcttgaaga aattaatgtg ttcaatgcag catcctccat catggttaat acattggttt   9120
aatttataca caaaattaaa caacatatta acacagtatc gatcaaatga ggttaaaaac   9180
catgggttta tattgataga taatcaaact cttagtggat ttcaatttat tttgaatcaa   9240
tatggttgta tagtttatca taaggaactc aaaagaatta ctgtgacaac ctataatcaa   9300
ttcttgacat ggaaagatat tagccttagt agattaaatg tttgtttaat tacatggatt   9360
agtaactgct tgaacacatt aaataaaagc ttaggcttaa gatgcggatt caataatgtt   9420
atcttgacac aactattcct ttatggtgat tgtatactaa agctatttca caatgagggg   9480
ttctacataa taaaagaggt agagggattt attatgtctc taattttaaa tataacagaa   9540
gaagatcaat tcagaaaacg attttataat agtatgctca acaacatcac agatgctgct   9600
aataaagctc agaaaaatct gctatcaaga gtatgtcata cattattaga taagacagta   9660
tccgataata taataaatgg cagatggata attctattaa gtaagttcct taaattaatt   9720
aagcttgcag gtgacaataa ccttaacaat ctgagtgaac tatatttttt gttcagaata   9780
tttggacacc caatggtaga tgaaagacaa gccatggatg ctgttaaagt taattgcaat   9840
gagaccaaat tttacttgtt aagcagtttg agtatgttaa gaggtgcctt tatatataga   9900
attataaaag ggtttgtaaa taattacaac agatggccta ctttaagaaa tgctattgtt   9960
ttacccttaa gatggttaac ttactataaa ctaaacactt atccttcttt gttggaactt  10020
acagaaagag atttgattgt gttatcagga ctacgtttct atcgtgagtt tcggttgcct  10080
aaaaaagtgg atcttgaaat gattataaat gataaagcta tatcaccccc taaaaatttg  10140
atatggacta gtttccctag aaattatatg ccgtcacaca tacaaaacta tatagaacat  10200
gaaaaattaa aattttccga gagtgataaa tcaagaagag tattagagta ttatttaaga  10260
gataacaaat tcaatgaatg tgatttatac aactgtgtag ttaatcaaag ttatctcaac  10320
aaccctaatc atgtggtatc attgacaggc aaagaaagag aactcagtgt aggtagaatg  10380
tttgcaatgc aaccgggaat gttcagacag gttcaaatat tggcagagaa aatgatagct  10440
gaaaacattt tacaattctt tcctgaaagt cttacaagat atggtgatct agaactacaa  10500
```

-continued

```
aaaatattag aattgaaagc aggaataagt aacaaatcaa atcgctacaa tgataattac  10560
aacaattaca ttagtaagtg ctctatcatc acagatctca gcaaattcaa tcaagcattt  10620
cgatatgaaa cgtcatgtat ttgtagtgat gtgctggatg aactgcatgg tgtacaatct  10680
ctattttcct ggttacattt aactattcct catgtcacaa taatatgcac atataggcat  10740
gcaccccct atataagaga tcatattgta gatcttaaca atgtagatga acaaagtgga  10800
ttatatagat atcacatggg tggtattgaa gggtggtgtc aaaaactatg gaccatagaa  10860
gctatatcac tattggatct aatatctctc aaagggaaat tctcaattac tgctttaatt  10920
aatggtgaca atcaatcaat agatataagc aaaccagtca gactcatgga aggtcaaact  10980
catgctcaag cagattattt gctagcatta aatagcctta aattactgta taaagagtat  11040
gcaggcatag gtcacaaatt aaaaggaact gagacttata tatcacgaga tatgcaattt  11100
atgagtaaaa caattcaaca taacggtgta tattaccctg ctagtataaa gaaagtccta  11160
agagtgggac cgtggataaa cactatactt gatgatttca aagtgagtct agaatctata  11220
ggtagtttga cacaagaatt agaatataga ggtgaaagtc tattatgcag tttaatattt  11280
agaaatgtat ggttatataa tcaaattgct ctacaattaa aaaatcatgc gttatgtaac  11340
aataaattat atttggacat attaaaggtt ctgaaacact taaaaacctt ttttaatctt  11400
gataatattg atacagcatt aacattgtat atgaatttac ccatgttatt tggtggtggt  11460
gatcccaact tgttatatcg aagtttctat agaagaactc ctgatttcct cacagaggct  11520
atagttcact ctgtgttcat acttagttat tatacaaacc atgacttaaa agataaactt  11580
caagatttgt cagatgatag attgaataag ttcttaacat gcataatcac gtttgacaaa  11640
aaccctaatg ctgaattcgt aacattgatg agagatcctc aagctttagg gtctgagaga  11700
caagctaaaa ttactagtga aatcaataga ctggcagtta cagaggtttt gagtacagct  11760
ccaaacaaaa tattctccaa aagtgcacaa cattatacca ctacagagat agatctaaat  11820
gatattatgc aaaatataga acctacatat cctcacgggc taagagttgt ttatgaaagt  11880
ttaccctttt ataaagcaga gaaaatagta aatcttatat caggtacaaa atctataact  11940
aacatactgg aaaagacttc tgccatagac ttaacagata ttgatagagc cactgagatg  12000
atgaggaaaa acataacttt gcttataagg atacttccat tggattgtaa cagagataaa  12060
agagaaatat tgagtatgga aaacctaagt attactgaat taagcaaata tgttagggaa  12120
agatcttggt ctttatccaa tatagttggt gttacatcac ccagtatcat gtatacaatg  12180
gacatcaaat atacaacaag cactatagct agtggcataa ttatagagaa atataatgtt  12240
aacagtttaa cacgtggtga gagaggacca actaaaccat gggttggttc atctacacaa  12300
gagaaaaaaa caatgccagt ttataataga caagttttaa ccaaaaaaca aagagatcaa  12360
atagatctat tagcaaaatt ggattgggtg tatgcatcta tagataacaa ggatgaattc  12420
atggaagaac tcagcatagg aacccttggg ttaacatatg aaaaggccaa aaaattattt  12480
ccacaatatt taagtgtcaa ctatttgcat cgccttacag tcagtagtag accatgtgaa  12540
ttccctgcat caataccagc ttatagaaca acaaattatc actttgacac tagccctatt  12600
aatcgcatat taacagaaaa gtatggtgat gaagatattg acatagtatt ccaaaactgt  12660
ataagctttg gccttagctt aatgtcagta gtagaacaat ttactaatgt atgtcctaac  12720
agaattattc tcatacctaa gcttaatgag atacatttga tgaaacctcc catattcaca  12780
ggtgatgttg atattcacaa gttaaaacaa gtgatacaaa aacagcatat gtttttacca  12840
gacaaaataa gtttgactca atatgtggaa ttattcttaa gtaacaaaac actcaaatct  12900
```

ggatctcatg ttaattctaa tttaatattg gcacataaaa tatctgacta ttttcataat 12960
acttacattt taagtactaa tttagctgga cattggattc taattataca acttatgaaa 13020
gattctaaag gtatttttga aaaagattgg ggagagggat atataactga tcatatgttt 13080
attaatttga aagttttctt caatgcttat aagacctatc tcttgtgttt tcataaaggt 13140
tatggcaaag caaaactgga gtgtgatatg aacacttcag atcttctatg tgtattggaa 13200
ttaatagaca gtagttattg gaagtctatg tctaaggtat ttttagaaca aaaagttatc 13260
aaatacattc ttagccaaga tgcaagttta catagagtaa aaggatgtca tagcttcaaa 13320
ttatggtttc ttaaacgtct taatgtagca gaatttacag tttgcccttg ggttgttaac 13380
atagattatc atccaacaca tatgaaagca atattaactt atatagatct tgttagaatg 13440
ggattgataa atatagatag aatacacatt aaaaataaac acaaattcaa tgatgaattt 13500
tatacttcta atctctttta cattaattat aacttctcag ataatactca tctattaact 13560
aaacatataa ggattgctaa ttcagaatta gaaaataatt acaacaaatt atatcatcct 13620
acaccagaaa ccctagagaa tatactagcc aatccgatta aaagtaatga caaaaagaca 13680
ctgaacgact attgtatagg taaaaatgtt gactcaataa tgttaccatt gttatctaat 13740
aagaagcttg ttaaatcgtc tgcaatgatt agaaccaatt acagcaaaca agacctgtac 13800
aatctattcc ctacggttgt gatcgataga attatagatc attcaggtaa tacagccaaa 13860
tccaaccaac tttacactac tacttcccat caaatatctt tagtgcacaa tagcacatca 13920
ctttattgca tgcttccttg gcatcatatt aatagattca attttgtatt tagttctaca 13980
ggttgtaaaa ttagtataga gtatatttta aaagacctta aaattaaaga tcctaattgt 14040
atagcattca taggtgaagg agcagggaat ttattattgc gtacagtggt ggaacttcat 14100
cctgacataa gatatattta cagaagtctg aaagattgca atgatcatag tttacctatt 14160
gagtttttaa ggctatacaa tggacatatc aacattgatt atggtgaaaa tttgaccatt 14220
cctgctacag atgcaaccaa caacattcat tggtcttatt tacatataaa gtttgctgaa 14280
cctatcagtc tttttgtatg tgatgccgaa ttgcctgtaa cagtcaactg gagtaaaatt 14340
ataatagaat ggagcaagca tgtaagaaaa tgcaagtact gttcctcagt taataaatgt 14400
acgttaatag taaaatatca tgctcaagat gatattgatt tcaaattaga caatataact 14460
atattaaaaa cttatgtatg cttaggcagt aagttaaagg gatcggaggt ttacttagtc 14520
cttacaatag gtcctgcaaa tatatttcca gtatttaatg tagtacaaaa tgctaaattg 14580
atactatcaa gaaccaaaaa tttcatcatg cctaagaaag ctgataaaga gtctattgat 14640
gcaaatatta aaagtttgat acccttcctt tgttacccta taacaaaaaa aggaattaat 14700
actgcattgt caaaactaaa gagtgttgtt agtggagata tactatcata ttctatagct 14760
ggacggaatg aagttttcag caataaactt ataaatcata agcatatgaa catcttaaag 14820
tggttcaatc atgttttaaa tttcagatca acagaactaa actataacca tttatatatg 14880
gtagaatcta catatcctta cctaagtgaa ttgttaaaca gcttgacaac taatgaactt 14940
aaaaaactga ttaaaatcac aggtagtctg ttatacaact ttcataatga ataatgaata 15000
aagatcttat aataaaaatt cctatagcta tacactagca ctgtattcaa ttatagttat 15060
taaaaaatta aaaatcatat aattttttat aaaaataact tttagtgaac taatcctaaa 15120
gttatcattt tgatctagga ggaataaatt taaatcccaa tctaattggt ttatatgtgt 15180
attaactaaa ctacgagata ttagtttttg acactttttt tctcgt 15226

<210> SEQ ID NO 119
<211> LENGTH: 15225
<212> TYPE: DNA
<213> ORGANISM: respiratory syncytial virus
<300> PUBLICATION INFORMATION:
<308> DATABASE ACCESSION NUMBER: AF013254.1
<309> DATABASE ENTRY DATE: 1997-11-02
<313> RELEVANT RESIDUES IN SEQ ID NO: (1)..(15225)

<400> SEQUENCE: 119
acgcgaaaaa atgcgtacta caaacttgca cattcggaaa aaatggggca aataagaatt 60
tgataagtgc tatttaagtc taacctttc aatcagaaat ggggtgcaat tcactgagca 120
tgataaaggt tagattacaa aatttatttg acaatgacga agtagcattg ttaaaaataa 180
catgttatac tgacaaatta attcttctga ccaatgcatt agccaaagca gcaatacata 240
caattaaatt aaacggtata gtttttatac atgttataac aagcagtgaa gtgtgccctg 300
ataacaacat tgtagtaaaa tctaacttta caacaatgcc aatattacaa aacggaggat 360
acatatggga attgattgag ttgacacact gctctcaatt aaacggtcta atggatgata 420
attgtgaaat caaattttct aaaagactaa gtgactcagt aatgactaat tatatgaatc 480
aaatatctga tttacttggg cttgatctca attcatgaat tatgtttagt ctaactcaat 540
agacatgtgt ttattaccat tttagttaat ataaaaactc atcaaaggga aatggggcaa 600
ataaactcac ctaatcaatc aaactatgag cactacaaat gacaacacta ctatgcaaag 660
attaatgatc acggacatga gacccctgtc gatggattca ataataacat ctctcaccaa 720
agaaatcatc acacacaaat tcatatactt gataaacaat gaatgtattg taagaaaact 780
tgatgaaaga caagctacat ttacattctt agtcaattat gagatgaagc tactgcacaa 840
agtagggagt accaaataca agaaatacac tgaatataat acaaaatatg gcactttccc 900
catgcctata tttatcaatc atggcgggtt tctagaatgt attggcatta agcctacaaa 960
acacactcct ataatataca aatatgacct caacccgtaa attccaacaa aaaaaaccaa 1020
cccaaccaaa ccaagctatt cctcaaacaa caatgctcaa tagttaagaa ggagctaatc 1080
cgttttagta attaaaaata aaagtaaagc caataacata aattggggca aatacaaaga 1140
tggctcttag caaagtcaag ttaaatgata cattaaataa ggatcagctg ctgtcatcca 1200
gcaaatacac tattcaacgt agtacaggag ataatattga cactcccaat tatgatgtgc 1260
aaaaacacct aaacaaacta tgtggtatgc tattaatcac tgaagatgca aatcataaat 1320
tcacaggatt aataggtatg ttatatgcta tgtccaggtt aggaagggaa gacactataa 1380
agatacttaa agatgctgga tatcatgtta aagctaatgg agtagatata acaacatatc 1440
gtcaagatat aaatggaaag gaaatgaaat tcgaagtatt aacattatca agcttgacat 1500
cagaaataca agtcaatatt gagatagaat ctagaaaatc ctacaaaaaa atgctaaaag 1560
agatgggaga agtggctcca gaatataggc atgattctcc agactgtggg atgataatac 1620
tgtgtatagc agcacttgta ataaccaaat tagcagcagg agacagatca ggtcttacag 1680
cagtaattag gagggcaaac aatgtcttaa aaaatgaaat aaaacgctac aagggtctca 1740
taccaaagga tatagctaac agtttttatg aagtgtttga aaaacaccct catcttatag 1800
atgtttttgt gcactttggc attgcacaat catcaacaag agggggtagt agagttgaag 1860
gaatctttgc aggattgttt atgaatgcct atggttcagg gcaagtaatg ctaagatggg 1920
gagttttagc caaatctgta aaaaatatca tgctaggtca tgctagtgtc caggcagaaa 1980
tggagcaagt tgtggaagtc tatgagtatg cacagaagtt gggaggagaa gctggattct 2040

-continued

```
accatatatt gaacaatcca aaagcatcat tgctgtcatt aactcaattt cctaacttct   2100
caagtgtggt cctaggcaat gcagcaggtc taggcataat gggagagtat agaggtacgc   2160
caagaaacca ggatctttat gatgcagcca aagcatatgc agagcaactc aaagaaaatg   2220
gagtaataaa ctacagtgta ttagacttaa cagcagaaga attggaagcc ataaagaatc   2280
aactcaaccc taaagaagat gatgtagagc tttaagttaa caaaaaatac ggggcaaata   2340
agtcaacatg gagaagtttg cacctgaatt tcatggagaa gatgcaaata acaaagctac   2400
caaattccta gaatcaataa agggcaagtt cgcatcatcc aaagatccta agaagaaaga   2460
tagcataata tctgttaact caatagatat agaagtaacc aaagagagcc cgataacatc   2520
tggcaccaac atcatcaatc caacaagtga agccgacagt accccagaaa ccaaagccaa   2580
ctacccaaga aaacccctag taagcttcaa agaagatctc accccaagtg acaacccttt   2640
ttctaagttg tacaaagaaa caatagaaac atttgataac aatgaagaag aatctagcta   2700
ctcatatgaa gagataaatg atcaaacaaa tgacaacatt acagcaagac tagatagaat   2760
tgatgaaaaa ttaagtgaaa tattaggaat gctccataca ttagtagttg caagtgcagg   2820
acccacttca gctcgcgatg gaataagaga tgctatggtt ggtctgagag aagaaatgat   2880
agaaaaaata agagcggaag cattaatgac caatgatagg ttagaggcta tggcaagact   2940
taggaatgag gaaagcgaaa aaatggcaaa agacacctca gatgaagtgc ctcttaatcc   3000
aacttccaaa aaattgagtg acttgttgga agacaacgat agtgacaatg atctgtcact   3060
tgatgatttt tgatcagtga tcaactcact cagcaatcaa caacatcaat aaaacagaca   3120
tcaatccatt gaatcaactg ccagaccgaa caaacaaatg tccgtcagcg gaaccaccaa   3180
ccaatcaatc aaccaactga tccatcagca acctgacgaa attaacaata tagtaacaaa   3240
aaaagaacaa gatggggcaa atatggaaac atacgtgaac aagcttcacg aaggctccac   3300
atacacagca gctgttcagt acaatgttct agaaaaagat gatgatcctg catcactaac   3360
aatatgggtg cctatgttcc agtcatctgt accagcagac ttgctcataa aagaacttgc   3420
aagcatcaac atactagtga agcagatctc tacgcccaaa ggaccttcac tacgagtcac   3480
gattaactca agaagtgctg tgctggctca aatgcctagt aatttcatca taagcgcaaa   3540
tgtatcatta gatgaaagaa gcaaattagc atatgatgta actacacctt gtgaaatcaa   3600
agcatgcagt ctaacatgct taaaagtgaa aagtatgtta actacagtca aagatcttac   3660
catgaagaca ttcaacccca ctcatgagat cattgctcta tgtgaatttg aaaatattat   3720
gacatcaaaa agagtaataa taccaaccta tctaagacca attagtgtca aaaacaagga   3780
tctgaactca ctagaaaaca tagcaaccac cgaattcaaa aatgctatca ccaatgcgaa   3840
aattattccc tatgctggat tagtattagt tatcacagtt actgacaata aaggagcatt   3900
caaatatatc aagccacaga gtcaatttat agtagatctt ggtgcctacc tagaaaaaga   3960
gagcatatat tatgtgacta ctaattggaa gcatacagct acacgttttt caatcaaacc   4020
actagaggat taaatttaat tatcaacact gaatgacagg tccacatata tcctcaaact   4080
acacactata tccaaacatc atgaacatct acactacaca cttcatcaca caaaccaatc   4140
ccactcaaaa tccaaaatca ctaccagcca ctatctgcta gacctagagt gcgaataggt   4200
aaataaaacc aaaatatggg gtaaatagac attagttaga gttcaatcaa tctcaacaac   4260
catttatacc gccaattcaa tacatatact ataaatctta aaatgggaaa tacatccatc   4320
acaatagaat tcacaagcaa attttggccc tattttacac taatacatat gatcttaact   4380
```

-continued

```
ctaatctctt tactaattat aatcactatt atgattgcaa tactaaataa gctaagtgaa   4440
cataaaacat tctgtaacaa tactcttgaa ctaggacaga tgcatcaaat caacacatag   4500
tgctctacca tcatgctgtg tcaaattata atcctgtata tataaacaaa caaatccaat   4560
cttctcacag agtcatggtg tcgcaaaacc acgccaacta tcatggtagc atagagtagt   4620
tatttaaaaa ttaacataat gatgaattat tagtatggga tcaaaaacaa cattggggca   4680
aatgcaacca tgtccaaaca caagaatcaa cgcactgcca ggactctaga aaagacctgg   4740
gatactctca atcatctaat tgtaatatcc tcttgtttat acagattaaa tttaaaatct   4800
atagcacaaa tagcactatc agttctggca atgataatct caacctctct cataattgca   4860
gccataatat tcatcatctc tgccaatcac aaagttacac taacaacggt cacagttcaa   4920
acaataaaaa accacactga aaaaaacatc accacctacc ttactcaagt cccaccagaa   4980
agggttagct catccaaaca acctacaacc acatcaccaa tccacacaaa ttcagccaca   5040
acatcaccca acacaaagtc agaaacacac cacacaacag cacaaaccaa aggcagaacc   5100
accacctcaa cacagaccaa caagccgagc acaaaaccac gcctaaaaaa tccaccaaaa   5160
aaaccaaaag atgattacca ttttgaagtg ttcaacttcg ttccctgtag tatatgtggc   5220
aacaatcaac tttgcaaatc catctgtaaa acaataccaa gcaacaaacc aaagaagaaa   5280
ccaaccatca aacccacaaa caaaccaacc accaaaacca caaacaaaag agacccaaaa   5340
acaccagcca aaacgacgaa aaaagaaact accaccaacc caacaaaaaa accaaccctc   5400
acgaccacag aaagagacac cagcacctca caatccactg tgctcgacac aaccacatta   5460
gaacacacaa tccaacagca atccctccac tcaaccaccc ccgaaaacac acccaactcc   5520
acacaaacac ccacagcatc cgagccctct acatcaaatt ccacccaaaa tacccaatca   5580
catgcttagt tattcaaaaa ctacatctta gcagaaaacc gtgacctatc aagcaagaac   5640
gaaattaaac ctggggcaaa taaccatgga gctgctgatc cacaggttaa gtgcaatctt   5700
cctaactctt gctattaatg cattgtacct cacctcaagt cagaacataa ctgaggagtt   5760
ttaccaatcg acatgtagtg cagttagcag aggttatttt agtgctttaa gaacaggttg   5820
gtataccagt gtcataacaa tagaattaag taatataaaa gaaaccaaat gcaatggaac   5880
tgacactaaa gtaaaactta taaaacaaga attagataag tataagaatg cagtgacaga   5940
attacagcta cttatgcaaa acacaccagc tgccaacaac cgggccagaa gagaagcacc   6000
acagtatatg aactatacaa tcaataccac taaaaaccta aatgtatcaa taagcaagaa   6060
gaggaaacga agatttctgg gcttcttgtt aggtgtagga tctgcaatag caagtggtat   6120
agctgtatcc aaagttctac accttgaagg agaagtgaac aagatcaaaa atgctttgtt   6180
atctacaaac aaagctgtag tcagtctatc aaatggggtc agtgttttaa ccagcaaagt   6240
gttagatctc aagaattaca taaataacca attattaccc atagtaaatc aacagagctg   6300
tcgcatctcc aacattgaaa cagttataga attccagcag aagaacagca gattgttgga   6360
aatcaacaga gaattcagtg tcaatgcagg tgtaacaaca cctttaagca cttacatgtt   6420
aacaaacagt gagttactat cattgatcaa tgatatgcct ataacaaatg atcagaaaaa   6480
attaatgtca agcaatgttc agatagtaag gcaacaaagt tattctatca tgtctataat   6540
aaaggaagaa gtccttgcat atgttgtaca gctacctatc tatggtgtaa tagatacacc   6600
ttgctggaaa ttacacacat cacctctatg caccaccaac atcaaagaag gatcaaatat   6660
ttgtttaaca aggactgata gaggatggta ttgtgataat gcaggatcag tatccttctt   6720
tccacaggct gacacttgta aagtacagtc caatcgagta ttttgtgaca ctatgaacag   6780
```

-continued

```
tttgacatta ccaagtgaag tcagcctttg taacactgac atattcaatt ccaagtatga   6840
ctgcaaaatt atgacatcaa aaacagacat aagcagctca gtaattactt ctcttggagc   6900
tatagtgtca tgctatggta aaactaaatg cactgcatcc aacaaaaatc gtgggattat   6960
aaagacattt tctaatggtt gtgactatgt gtcaaacaaa ggagtagata ctgtgtcagt   7020
gggcaacact ttatactatg taaacaagct ggaaggcaag aacctttatg taaaagggga   7080
acctataata aattactatg accctctagt gtttccttct gatgagtttg atgcatcaat   7140
atctcaagtc aatgaaaaaa tcaatcaaag tttagctttt attcgtagat ctgatgaatt   7200
actacataat gtaaatactg gcaaatctac tacaaatatt atgataacta caattattat   7260
agtaatcatt gtagtattgt tatcattaat agctattggt ttgctgttgt attgcaaagc   7320
caaaaacaca ccagttacac taagcaaaga ccaactaagt ggaatcaata atattgcatt   7380
cagcaaatag acaaaaaacc acctgatcat gtttcaacaa cagtctgctg atcaccaatc   7440
ccaaatcaac ccataacaaa cacttcaaca tcacagtaca ggctgaatca tttcttcaca   7500
tcatgctacc cacacaacta agctagatcc ttaactcata gttacataaa aacctcaagt   7560
atcacaatca aacactaaat caacacatca ttcacaaaat taacagctgg ggcaaatatg   7620
tcgcgaagaa atccttgtaa atttgagatt agaggtcatt gcttgaatgg tagaagatgt   7680
cactacagtc ataattactt tgaatggcct cctcatgcct tactagtgag gcaaaacttc   7740
atgttaaaca agatactcaa gtcaatggac aaaagcatag acactttgtc tgaaataagt   7800
ggagctgctg aactggacag aacagaagaa tatgctcttg gtatagttgg agtgctagag   7860
agttacatag gatctataaa caacataaca aaacaatcag catgtgttgc tatgagtaaa   7920
cttcttattg agatcaatag tgatgacatt aaaaagctga gagataatga agaacccaat   7980
tcacctaaga taagagtgta caatactgtt atatcataca ttgagagcaa tagaaaaaac   8040
aacaagcaaa caatccatct gctcaaaaga ctaccagcag acgtgctgaa gaagacaata   8100
aaaaacacat tagatatcca caaaagcata atcataagca acccaaaaga gtcaaccgtg   8160
aatgatcaaa atgaccaaac caaaaataat gatattaccg gataaatatc cttgtagtat   8220
atcatccata ttgatttcaa gtgaaagcat gattgctaca ttcaatcata aaaacatatt   8280
acaatttaac cataaccatt tggataacca ccagcgttta ttaaataata tatttgatga   8340
aattcattgg acacctaaaa acttattaga tgccactcaa caatttctcc aacatcttaa   8400
catccctgaa gatatatata caatatatat attagtgtca taatgcttgg ccataacgat   8460
tctatatcat ccaaccataa aactatctta ataaggttat gggacaaaat ggatcccatt   8520
attaatggaa actctgctaa tgtgtatcta actgatagtt atttaaaagg tgttatctct   8580
ttttcagaat gtaatgcttt agggagttac cttttttaacg gcccttatct caaaaatgat   8640
tacaccaact taattagtag acaaagtcca ctactagagc atatgaatct taaaaaacta   8700
actataacac agtcattaat atctagatat cataaaggtg aactgaaatt agaagaacca   8760
acttatttcc agtcattact tatgacatat aaaagcatgt cctcgtctga acaaattgct   8820
acaactaact tacttaaaaa aataatacga agagctatag aaataagtga tgtaaaggtg   8880
tacgccatct tgaataaact aggactaaag gaaaaggaca gagttaagcc caacaataat   8940
tcaggtgatg aaaactcagt acttacaact ataattaaag atgatatact ttcggctgtg   9000
gaaagcaatc aatcatatac aaattcagac aaaaatcact cagtaaatca aaatatcact   9060
atcaaaacaa cactcttgaa aaaattgatg tgttcaatgc aacatcctcc atcatggtta   9120
```

-continued

```
atacactggt tcaatttata tacaaaatta aataacatat taacacaata tcgatcaaat   9180
gaggtaaaaa gtcatgggtt tatattaata gataatcaaa ctttaagtgg ttttcagttt   9240
attttaaatc aatatggttg tatcgtttat cataaaggac tcaaaaaaat cacaactact   9300
acttacaatc aatttttaac atggaaagac atcagcctta gcagattaaa tgtttgctta   9360
attacttgga taagtaattg tttgaataca ttaaataaaa gcttagggct gagatgtgga   9420
ttcaataatg ttgtgttatc acaattattt ctttatggag attgtatact gaaattattt   9480
cataatgaag gcttctacat aataaaagaa gtagagggat ttattatgtc tttaattcta   9540
aacataacag aagaagatca atttaggaaa cgattttata atagcatgct aaataacatc   9600
acagatgcag ctattaaggc tcaaaagaac ctactatcaa gggtatgtca cactttatta   9660
gacaagacag tgtctgataa tatcataaat ggtaaatgga taatcctatt aagtaaattt   9720
cttaaattga ttaagcttgc aggtgataat aatctcaata atttgagtga gctatatttt   9780
ctcttcagaa tctttggaca tccaatggtt gatgaaagac aagcaatgga tgctgtaaga   9840
attaactgta atgaaactaa gttctactta ttaagtagtc taagtacgtt aagaggtgct   9900
ttcatttata gaatcataaa agggtttgta aatacctaca acagatggcc cactttaagg   9960
aatgctattg tcctacctct aagatggtta aactattata aacttaatac ttatccatct  10020
ctacttgaaa tcacagaaaa tgatttgatt attttatcag gattgcggtt ctatcgtgaa  10080
tttcatctgc ctaaaaaagt ggatcttgaa atgataataa atgacaaagc catttcacct  10140
ccaaaagatc taatatggac tagttttcct agaaattaca tgccatcaca tatacaaaat  10200
tatatagaac atgaaaagtt gaagttctct gaaagcgaca gatcaagaag agtactagag  10260
tattacttga gagataataa attcaatgaa tgcgatctat acaattgtgt agtcaatcaa  10320
agctatctca acaactctaa tcacgtggta tcactaactg gtaaagaaag agagctcagt  10380
gtaggtagaa tgtttgctat gcaaccaggt atgtttaggc aaatccaaat cttagcagag  10440
aaaatgatag ccgaaaatat tttacaattc ttccctgaga gtttgacaag atatggtgat  10500
ctagagcttc aaaagatatt agaattaaaa gcaggaataa gcaacaagtc aaatcgttat  10560
aatgataact acaacaatta tatcagtaaa tgttctatca ttacagatct tagcaaattc  10620
aatcaagcat ttagatatga aacatcatgt atctgcagtg atgtattaga tgaactgcat  10680
ggagtacaat ctctgttctc ttggttgcat ttaacaatac ctcttgtcac aataaatatgt  10740
acatatagac atgcacctcc tttcataaag gatcatgttg ttaatcttaa tgaagttgat  10800
gaacaaagtg gattatacag atatcatatg ggtggtattg agggctggtg tcaaaaactg  10860
tggaccattg aagctatatc attattagat ctaatatctc tcaaagggaa attctctatc  10920
acagctctga taaatggtga taatcagtca attgatataa gtaaaccagt tagacttata  10980
gagggtcaga cccatgctca agcagattat ttgttagcat taaatagcct taaattgcta  11040
tataaagagt atgcaggtat aggccataag cttaagggaa cagagaccta tatatcccga  11100
gatatgcagt tcatgagcaa aacaatccag cacaatggag tgtactatcc agccagtatc  11160
aaaaaagtcc tgagagtagg tccatggata aatacaatac ttgatgattt taaagttagt  11220
ttagaatcta taggtagctt aacacaggag ttagaataca gaggggaaag cttattatgc  11280
agtttaatat ttaggaacat ttggttatac aatcaaattg ctttgcaact ccgaaatcat  11340
gcattatgta acaataagct atatttagat atattgaaag tattaaaaca cttaaaaact  11400
ttttttaatc ttgatagtat cgatatggcg ttatcattgt atatgaattt gcctatgctg  11460
tttggtggtg gtgatcctaa tttgttatat cgaagctttt ataggagaac tccagacttc  11520
```

-continued

```
cttacagaag ctatagtaca ttcagtgttt gtgttgagct attatactgg tcacgattta  11580
caagataagc tccaggatct tccagatgat agactgaaca aattcttgac atgtgtcatc  11640
acattcgata aaaatcccaa tgccgagttt gtaacattga tgagggatcc acaggcgtta  11700
gggtctgaaa ggcaagctaa aattactagt gagattaata gattagcagt aacagaagtc  11760
ttaagtatag ctccaaacaa aatattttct aaaagtgcac aacattatac taccactgag  11820
attgatctaa atgacattat gcaaaatata gaaccaactt accctcatgg attaagagtt  11880
gtttatgaaa gtctaccttt ttataaagca gaaaaaatag ttaatcttat atcaggaaca  11940
aaatccataa ctaatatact tgaaaaaaca tcagcaatag atacaactga tattaatagg  12000
gctactgata tgatgaggaa aaatataact ttacttataa ggatacttcc actagattgt  12060
aacaaagaca aaagagagtt attaagttta gaaaatctta gtataactga attaagcaag  12120
tatgtaagag aaagatcttg gtcattatcc aatatagtag gagtaacatc gccaagtatt  12180
atgttcacaa tggacattaa atatacaact agcactatag ccagtggtat aattatagaa  12240
aaatataatg ttaatagttt aactcgtggt gaaagaggac ctactaagcc atgggtaggt  12300
tcatctacgc aggagaaaaa aacaatgcca gtgtacaata gacaagtttt aaccaaaaag  12360
caaagagacc aaatagattt attagcaaaa ttagactggg tatatgcatc catagacaac  12420
aaagatgaat tcatggaaga actgagtact ggaacacttg gactgtcata tgaaaaagcc  12480
aaaaagttgt ttccacaata tctaagtgtc aattatttac accgtttaac agtcagtagt  12540
agaccatgtg aattccctgc atcaatacca gcttatagaa caacaaatta tcatttcgat  12600
actagtccta tcaatcatgt attaacagaa aagtatggag atgaagatat cgacattgtg  12660
tttcaaaatt gcataagttt tggtcttagc ctgatgtcgg ttgtggaaca attcacaaac  12720
atatgtccta atagaattat tctcataccg aagctgaatg agatacattt gatgaaacct  12780
cctatattta caggagatgt tgatatcatc aagttgaagc aagtgataca aaaacagcat  12840
atgttcctac cagataaaat aagtttaacc caatatgtag aattattcct aagtaacaaa  12900
gcacttaaat ctggatctaa catcaattct aatttaatat tagtacataa aatgtctgat  12960
tattttcata atgcttatat tttaagtact aatttagctg gacattggat tctaattatt  13020
caacttatga aagattcaaa aggtattttt gaaaaagatt ggggagaggg gtacataact  13080
gatcatatgt tcattaattt gaatgttttc tttaatgctt ataagactta tttgctatgt  13140
tttcataaag gttatggtaa agcaaaatta gaatgtgata tgaacacttc agatcttctt  13200
tgtgttttgg agttaataga cagtagctac tggaaatcta tgtctaaagt tttcctagaa  13260
caaaaagtca taaaatacat agtcaatcaa gacacaagtt tgcatagaat aaaaggctgt  13320
cacagtttta agttgtggtt tttaaaacgc cttaataatg ctaaatttac cgtatgccct  13380
tgggttgtta acatagatta tcacccaaca catatgaaag ctatattatc ttacatagat  13440
ttagttagaa tggggttaat aaatgtagat aaattaacca ttaaaaataa aaacaaattc  13500
aatgatgaat tttacacatc aaatctcttt tacattagtt ataacttttc agacaacact  13560
catttgctaa caaaacaaat aagaattgct aattcagaat tagaagataa ttataacaaa  13620
ctatatcacc caaccccaga aactttagaa aatatatcat taattcctgt taaaagtaat  13680
aatagtaaca aacctaaatt ttgtataagt ggaaataccg aatctataat gatgtcaaca  13740
ttctctaata aaatgcatat taaatcttcc actgttacca caagattcaa ttatagcaaa  13800
caagacttgt acaatttatt tccaaatgtt gtgatagaca ggattataga tcattcaggt  13860
```

-continued

```
aatacagcaa aatctaacca actttacatc accacttcac atcagacatc tttagtaagg  13920

aatagtgcat cactttattg catgcttcct tggcatcatg tcaatagatt taactttgta  13980

tttagttcca caggatgcaa gatcagtata gagtatattt taaaagatct taagattaag  14040

gaccccagtt gtatagcatt cataggtgaa ggagctggta acttattatt acgtacggta  14100

gtagaacttc atccagacat aagatacatt tacagaagtt taaaagattg caatgatcat  14160

agtttaccta ttgaatttct aagattatac aacgggcata taaacataga ttatggtgag  14220

aatttaacca ttcctgctac agatgcaact aataacattc attggtctta tttacatata  14280

aaatttgcag aacctattag catctttgtc tgcgatgctg aattacctgt tacagccaat  14340

tggagtaaaa ttataattga atggagtaag catgtaagaa agtgcaagta ctgttcttct  14400

gtaaatagat gcattttaat cgcaaaatat catgctcaag atgatattga tttcaaatta  14460

gataacatta ctatattaaa aacttacgtg tgcctaggta gcaagttaaa aggatctgaa  14520

gtttacttag tccttacaat aggccctgca aatatacttc ctgtttttga tgttgtgcaa  14580

aatgctaaat tgattttttc aagaactaaa aatttcatta tgcctaaaaa aactgacaag  14640

gaatctatcg atgcaaatat taaaagctta atacctttcc tttgttaccc tataacaaaa  14700

aaaggaatta agacttcatt gtcaaaattg aagagtgtag ttaatgggga tatattatca  14760

tattctatag ctggacgtaa tgaagtattc agcaacaagc ttataaacca caagcatatg  14820

aatatcctaa aatggctaga tcatgtttta aattttagat cagctgaact taattacaat  14880

catttataca tgatagagtc cacatatcct tacttaagtg aattgttaaa tagtttaaca  14940

accaatgagc tcaagaaact gattaaaata acaggtagtg tactatacaa ccttcccaac  15000

gaacagtaac ttaaaatatc attaacaagt ttggtcaaat ttagatgcta acacatcatt  15060

atattatagt tattaaaaaa tatgcaaact tttcaataat ttagcttact gattccaaaa  15120

ttatcatttt atttttaagg ggttgaataa aagtctaaaa ctaacaatga tacatgtgca  15180

tttacaacac aacgagacat tagtttttga cacttttttt ctcgt                 15225
```